(12) United States Patent
Black et al.

(10) Patent No.: US 10,383,958 B2
(45) Date of Patent: Aug. 20, 2019

(54) POLYMALIC ACID BASED NANOCONJUGATES FOR IMAGING

(75) Inventors: Keith L. Black, Los Angeles, CA (US); Julia Ljubimova, Studio City, CA (US); Alexander Ljubimov, Studio City, CA (US); Eggehard Holler, Los Angeles, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 369 days.

(21) Appl. No.: 13/441,599

(22) Filed: Apr. 6, 2012

(65) Prior Publication Data

US 2012/0258049 A1    Oct. 11, 2012

Related U.S. Application Data

(60) Provisional application No. 61/472,362, filed on Apr. 6, 2011.

(51) Int. Cl.
| | | |
|---|---|---|
| *A61K 49/16* | (2006.01) | |
| *A61K 49/12* | (2006.01) | |
| *A61K 47/59* | (2017.01) | |

(52) U.S. Cl.
CPC ............ *A61K 49/16* (2013.01); *A61K 47/593* (2017.08); *A61K 49/128* (2013.01)

(58) Field of Classification Search
None
See application file for complete search history.

(56) References Cited

U.S. PATENT DOCUMENTS

| | | | |
|---|---|---|---|
| 7,547,511 B2 | 6/2009 | Ljubimova et al. | |
| 7,935,677 B2 | 5/2011 | Ljubimova et al. | |
| 2002/0155440 A1* | 10/2002 | Ljubimova | C12Q 1/6886 435/6.16 |
| 2005/0074403 A1 | 4/2005 | Kayyem et al. | |
| 2006/0063209 A1 | 3/2006 | Meares et al. | |
| 2007/0066665 A1 | 3/2007 | Yang et al. | |
| 2007/0128118 A1* | 6/2007 | Yu | A61K 47/48238 424/9.322 |
| 2007/0165920 A1* | 7/2007 | Gering | A61B 5/055 382/128 |
| 2007/0259008 A1* | 11/2007 | Ljubimova | A61K 47/482 424/400 |
| 2009/0220431 A1* | 9/2009 | Cheon et al. | 424/9.32 |
| 2009/0263379 A1 | 10/2009 | Ljubimova et al. | |
| 2011/0020371 A1 | 1/2011 | Ding et al. | |
| 2011/0274617 A1* | 11/2011 | Abulrob | A61K 49/0002 424/1.21 |
| 2012/0207681 A1* | 8/2012 | Verdooner | 424/9.1 |

FOREIGN PATENT DOCUMENTS

| | | |
|---|---|---|
| CN | 101564540 A | 10/2009 |
| DE | 19808079 A1 | 8/1999 |
| WO | 9610359 A1 | 4/1996 |
| WO | 9611712 A2 | 4/1996 |
| WO | 2004071536 A1 | 8/2004 |
| WO | 2005028617 A2 | 3/2005 |
| WO | 2005055980 A2 | 6/2005 |
| WO | 2007064175 A1 | 6/2007 |
| WO | WO 2008124735 A2 * | 10/2008 ....... A61K 47/48215 |
| WO | 2009126913 A1 | 10/2009 |
| WO | WO 2009/126913 * | 10/2009 |
| WO | WO 2009157561 A1 * | 12/2009 |
| WO | 2011072240 A1 | 6/2011 |
| WO | 2011119588 A1 | 9/2011 |
| WO | 2012078647 A2 | 6/2012 |
| WO | 2012091718 A1 | 7/2012 |

OTHER PUBLICATIONS

WO2009157561 trans, "Translation of WO2009157561", printed Sep. 30, 2013.*
Wu, G., et al., "Targeted delivery of methotrexate to epidermal growth factor receptor-positive brain tumors by means of cetuximab (IMC-C225) dendrimer bioconjugates", 2006, Mol. Cancer. Therap., pp. 52-59.*
Heyn, C., et al., "In Vivo MRI of Cancer Cell Fate at the Single-Cell Level in a Mouse Model of Breast Cancer Metastasis to the Brain", Mag. Res. Med., 2006, pp. 1001-1010.*
Ljubimova, J. Y., et al., "Poly(malic acid) nanoconjugates containing various antibodies and oligonucleotides for multitargeting drug delivery", Nanomedicine, 2008, pp. 247-265.*
Andrew B. Newberg, et al., "Safety, Biodistribution, and Dosimetry of 123I-IMPY: A Novel Amyloid Plaque-Imaging Agent for the Diagnosis of Alzheimer's Disease", Journal of Nuclear Medicine, 2006, 47(5):748-754.
William E. Klunk, et al., "Imaging Brain Amyloid in Alzheimer's Disease with Pittsburgh Compound-B", Annals of Neurology, 2004, 55(3):306-319.
Bong-Seop Lee, et al., "Water-soluble Aliphatic Polyesters: Poly(malic acid)s", Biopolymers, 2002, 3a(Polyesters):76-103.
L.W. Seymour, et al., "Influence of Molecular Weight on Passive Tumour Accumulation of a Soluble Macromolecular Drug Carrier", European Journal of Cancer, 1995, 31A(5):766-770.
Jae H. Lee, et al., "Receptor mediated uptake of peptides that bind the human transferrin receptor", European Journal of Biochemistry, 2001, 268(7):2004-2012.
M. Kovar, et al., "In Vitro and In Vivo Effect of HPMA Copolymer-bound Doxorubicin Targeted to Transferrin Receptor of B-cell Lymphoma 38C13", Journal of Drug Targeting, 2002, 10(1):23-30.
Silvia Arpicco, et al., "Novel Poly(ethylene glycol) Derivatives for Preparation of Ribosome-Inactivating Protein Conjugates", Bioconjugate Chemistry, 2002, 13(4):757-765.
Kazuo Maruyama, et al., "Immunoliposomes bearing polyethyleneglycol-coupled Fab' fragment show prolonged circulation time and high extravasation into targeted solid tumors in vivo", Federation of European Biochemical Societies Letters, 1997, 413(1):177-180.

(Continued)

*Primary Examiner* — Michael G. Hartley
*Assistant Examiner* — Lance W Rider
(74) *Attorney, Agent, or Firm* — Volpe and Koenig, P.C.

(57) ABSTRACT

Nanoconjugates that include a polymalic-based molecular scaffold with one or more imaging moiety and one or more targeting modules attached to the scaffold are provided. Methods of targeting a diseased cell or a diseased tissue in a subject by administering the nanoconjugate are described. Methods of synthesizing the nanoconjugate are also provided.

12 Claims, 18 Drawing Sheets
(1 of 18 Drawing Sheet(s) Filed in Color)

(56) References Cited

OTHER PUBLICATIONS

Julia Y. Ljubimova, et al., "Nanoconjugate based on polymalic acid for tumor targeting", Chemico-Biological Interactions, 2008, 171(2):195-203.

Gill Marshall, et al., "Adverse events caused by MRI contrast agents: Implications for radiographers who inject", Radiography, 2012, 18(2):132-136.

Jia-Jyun Lin, et al., "Folic acid-Pluronic F127 magnetic nanoparticle clusters for combined targeting, diagnosis, and therapy applications", Biomaterials, 2009, 30(28):5114-5124.

Ewelina Kluza, et al., "Dual-targeting of alpha v beta 3 and galectin-1 improves the specificity of paramagnetic/fluorescent liposomes to tumor endothelium in vivo", Journal of Controlled Release, 2012, 15(2):207-214.

Tao Chen, et al., "Smart Multifunctional Nanostructure for Targeted Cancer Chemotherapy and Magnetic Resonance Imaging", ACS Nano, 2011, 5(10):7866-7873.

Ting-Jung Chen, et al., "Targeted Herceptin-dextran iron oxide nanoparticles for noninvasive imaging of HER2/neu receptors using MRI", Journal of Biological Inorganic Chemistry, 2009, 14(2):253-260.

Boguslaw Tomanek, et al., "Evaluation of brain tumor vessels specific contrast agents for glioblastoma imaging", Neuro-Oncology, 2012, 14(1):53-63.

Ruth Duncan, "Polymer conjugates for tumour targeting and intracytoplasmic delivery. The EPR effect as a common gateway?", Pharmaceutical Science & Technology Today, 1999, 2(11):441-449.

Scott Raymond, et al., "Ultrasound Enhanced Delivery of Molecular Imaging and Therapeutic Agents in Alzheimer's Disease Mouse Models", 2008, PLoS ONE 3(5):1-7.

Lee, et al., "Polycefin, a New Prototype of a Multifunctional Nanoconjugate Based on Poly(B-L-malic acid for Drug Delivery," Bioconjugate Chemistry, 2006, 17(2):317-326.

Ding, Hui et al. "Inhibition of brain tumor growth by intravenous poly (-L-malic) acid nanobioconjugate with pH-dependent drug release"; Proceedings of the National Academy of Sciences, vol. 107, No. 42, pp. 18143-18148 (Oct. 19, 2010) with Correction in vol. 107, No. 45, p. 19603 (Nov. 9, 2010).

Inoue, Satoshi et al. "Newly designed nanobioconjugate for direct targeting and systemic treatment of HER2-positive breast cancer"; Cancer Research; Proceedings: AACR 101st Annual Meeting 2010; Walter E. Washington Convention Center, Washington, D.C.; Abstract No. 3854; vol. 70, No. 8, suppl., one page (Apr. 1, 2010).

Inoue, Satoshi et al. "Polymalic Acid-Based Nanobiopolymer Provides Efficient Systemic Breast Cancer Treatment by Inhibiting both HER2/neu Receptor Synthesis and Activity"; Cancer Research, vol. 71, No. 4; pp. 1454-1464 (Feb. 8, 2011).

Ljubimova, Julia Y. et al. "Molecular Oncology"; Internet citation, XP008143608 (Jul. 1, 2009). Retrieved from the Internet:URL:http://www.cedars-sinai.edu/10141.html (retrieved on Sep. 29, 2011).

Supplementary European Search Report, European Patent Application No. 12768248.2; dated May 9, 2014 (11 pages).

\* cited by examiner

Clinical Gadolinium 15 min.
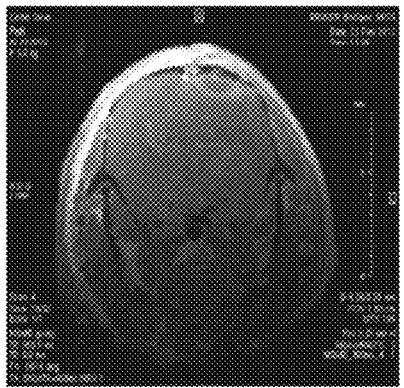
Clinical Gadolinium 1h 40 min.
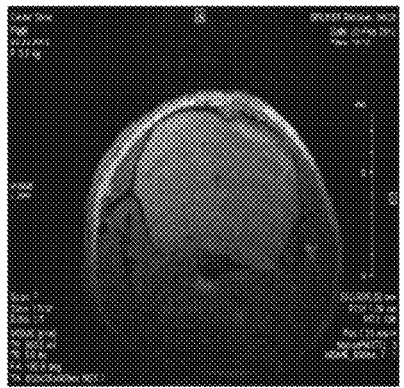
P/Gd-DOTA/MsTfR/Cetux/Alx680 15 min.
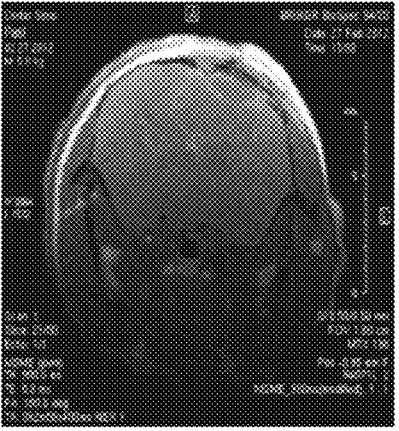
P/Gd-DOTA/MsTfR/Cetux/Alx680 3h 15 min.
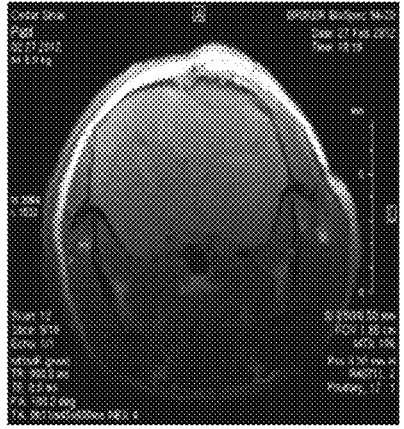
FIG. 9

Model: Metastatic triple-negative breast tumor in brain

Fluorescence (Xenogen) Imaging with "Gd-DOTA-Polycefin-AlexaFluor 680"

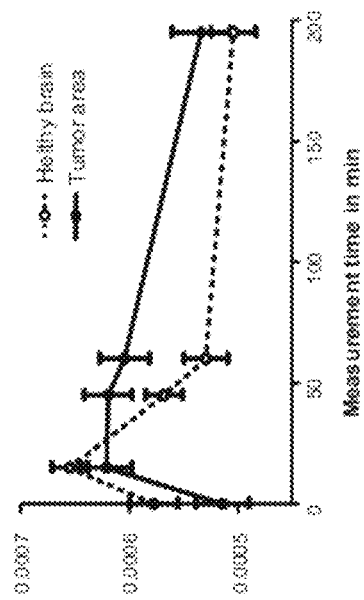
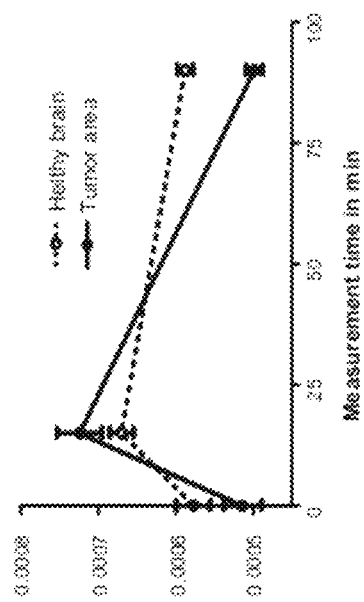
FIG. 12A
FIG. 12B

POLYMALIC ACID BASED NANOCONJUGATES FOR IMAGING

This application claims the benefit of U.S. Provisional Application No. 61/472,362, filed Apr. 6, 2011, which is incorporated by reference as if fully set forth.

STATEMENT REGARDING FEDERALLY SPONSORED RESEARCH OR DEVELOPMENT

The invention was made with government support under Grant No. CA123495 and Grant No. CA151815 awarded by National Institutes of Health. The government has certain rights in the invention.

FIELD OF INVENTION

The disclosure relates to nanoconjugates containing imaging moieties and targeting modules attached to a polymalic acid-based molecular scaffold. The disclosure also relates to methods of synthesizing nanoconjugates and targeting the diseased cells or tissues in by administering nanoconjugates to a subject.

BACKGROUND

Diagnostic imaging allows avoidance of unnecessary invasive surgical interventions by confirmation of the nature of various pathological conditions including differentiating between edema and a tumor, detection of multiple metastases, or detection of mental illness or dementia. Non-invasive imaging may be especially useful for diagnostics of diseases or pathological conditions of the human brain, which is not easily accessible by many conventional probing methods such as biopsy and light imaging. Non-invasive imaging is also needed for diagnosis of Alzheimer disease (AD), the most common form of dementia observed in people over 65 years of age.

The oldest approach to diagnose the AD was demonstration of Alzheimer's plaques in human tissue post mortem by employing small chemical compounds that attached specifically to the plaques and that could be visualized by staining ex vivo or by radioactive scintigram in vivo (Newberg A B et al. 2006 J Nuc Med 47:748).

After mouse models became available for AD and cancers, such as triple negative breast cancer, HER2-positive breast cancer, and glioblastoma, in vivo imaging methods could be developed. In vivo imaging approaches utilized fluorescent agents or tagged antibodies binding specifically to components of the diseased cells or tissues, or employed positron emission tomography (PET; Raymond S B et al. 2008 Plos One 3:e2175, 1; Klunk W E et al. 2004 Annals Neurol 55:306).

Although some of these approaches could demonstrate the existence of the diseased tissues, applications required long exposure times and were of insufficient resolution for clearly distinguishing details, or small Alzheimer's plaques. Breakthrough imaging techniques made use of magnetic resonance imaging (MRI). MRI is one of the most advanced non-invasive imaging systems due to application of high resolution contrast agents that include gadolinium (Gd). However, MRI fails to differentiate pathological conditions occurring within a brain. For example, MRI cannot distinguish cancer types, or even cancer from other malignancies. An inefficiency of many in vivo imaging approaches, including MRI, stems from the inability of the contrasting agents, such as gadolinium, to cross the blood-brain barrier (BBB) in combination with rapid elimination of the contrast agent through the kidneys.

SUMMARY

In an aspect, the invention relates to a nanoconjugate that includes a polymalic acid-based molecular scaffold, at least one imaging moiety and at least one targeting module. One or more of the at least one imaging moiety and one or more of the at least one targeting module is conjugated to the polymalic-acid based molecular scaffold.

In an aspect, the invention relates to a kit for facilitating imaging of a cell or a tissue in a subject. The kit contains a nanoconjugate that includes a polymalic acid-based molecular scaffold, at least one imaging moiety and at least one targeting module. One or more of the at least one imaging moiety and one or more of the at least one targeting module is conjugated to the polymalic-acid based molecular scaffold.

In an aspect, the invention relates to a method of targeting a cell or a tissue in a subject. The method includes administering to the subject a composition that includes a polymalic acid-based molecular scaffold, at least one imaging moiety and at least one targeting module. One or more of the at least one imaging moiety and one or more of the at least one targeting module is conjugated to the polymalic-acid based molecular scaffold.

In an aspect, the invention relates to a method of synthesizing a nanoconjugate. The method involves providing a polymalic acid having a plurality of pendant carboxyl groups. The method further involves reacting a compound containing sulfhydryl groups and amino acid groups through the pendant carboxyl groups to add sulfhydryl groups to the polymalic acid to form an activated polymalic acid. The method involves reacting at least one imaging moiety containing a sulfhydryl binding group to the activated polymalic acid to form a preconjugate. The method also involves reacting at least one targeting module containing a sulfhydryl binding group to the preconjugate.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description of the preferred embodiments will be better understood when read in conjunction with the appended drawings. For the purpose of illustration, there are shown in the drawings embodiments which are presently preferred. It is understood, however, that the invention is not limited to the precise arrangements and instrumentalities shown. In the drawings:

FIG. 9 is a set of MRI images showing tumors in brain sections of mice having TNBC metastatic tumors. Top images were taken 15 minutes (left) and 1 hour 45 minutes (right) after administering commercially available Gd(III) enhancer reagent to animals. Bottom images were taken 15 minutes (left) and 3 hours 15 minutes (right) after administering to animals a Polycefin nanoconjugate containing polymalic acid, Gd-DOTA, MsTfR, Cetuximab and Alexa Fluor 680 dye. Scale bar=50 µm.

FIGS. 12A and 12B illustrate MRI kinetics for parts of the brain having tumor (solid line) in comparison with healthy parts of the brain (broken line) after injecting to the subjects clinically used Gd(III) (FIG. 12A) and a Gd-DOTA-Polycefin nanoconjugate containing Gd-DOTA, MsTfR, Cetuximab and Alexa Fluor 680 (FIG. 12B).

DETAILED DESCRIPTION OF THE PREFERRED EMBODIMENTS

Figure 1:
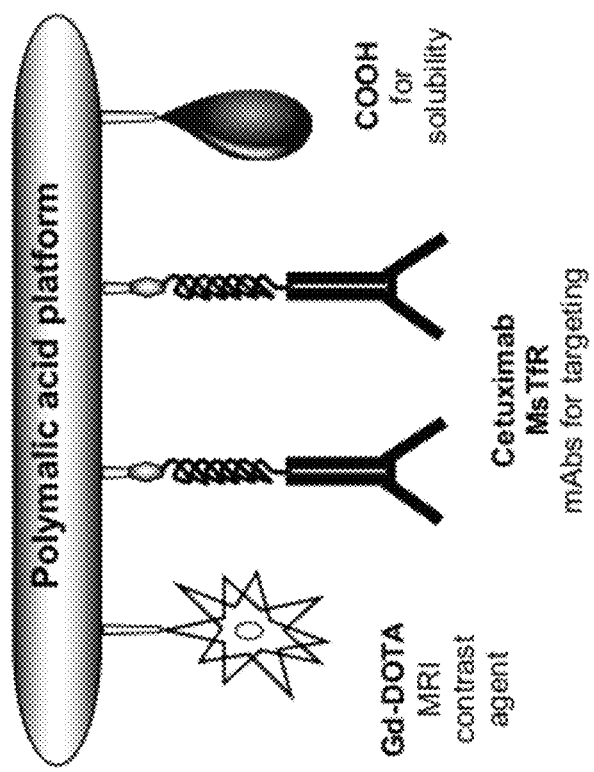
FIG. 1 is a schematic drawing illustrating a nanoconjugate designed to facilitate imaging of triple negative breast cancer (TNBC) metastasized to brain.

Certain terminology is used in the following description for convenience only and is not limiting. The words "right," "left," "top," and "bottom" designate directions in the drawings to which reference is made.

The words "a" and "one," as used in the claims and in the corresponding portions of the specification, are defined as including one or more of the referenced item unless specifically stated otherwise. This terminology includes the words above specifically mentioned, derivatives thereof, and words of similar import. The phrase "at least one" followed by a list of two or more items, such as "A, B, or C," means any individual one of A, B or C as well as any combination thereof.

An embodiment provides a nanoconjugate that may include a polymalic acid-based molecular scaffold, one or more imaging moieties and one or more targeting modules. At least one of the imaging moieties and at least one of the targeting modules may be conjugated to the polymalic acid-based molecular scaffold. All of the imaging moieties may be conjugated to the polymalic acid-based molecular scaffold. All of the targeting modules may be conjugated to the polymalic acid-based molecular scaffold.

Conjugated means covalently bound.

In an embodiment, the nanoconjugate may be Polycefin. As used herein, the term "Polycefin" refers to a family of compounds based on a polymalic acid as the platform for attachment of various specific residues for therapeutic targeting. Polycefin may include polymalic acid derived from a slime mold. Polycefin may be 20 to 30 nm in size and may act as a drug. Polycefin may be engineered to transport other therapeutic molecules. The polymalic acid (PMLA) may include a homopolymer that contains a main chain ester linkage. The polymalic acid may be obtained from cultures of *Physarum polycefallum*. The polymalic acid may be of any length and of any molecular mass. The polymalic acid may have a molecular mass of 10, 20, 30, 40, 50, 60, 70, 80, 90, 95, or 100 kDa, or more. The polymalic acid may have a molecular mass in a range between any two of the following molecular masses: 10, 20, 30, 40, 50, 60, 70, 80, 90, 95, or 100 kDa. The polymalic acid may be at least one of biodegradable and of a high molecular flexibility, soluble in water (when ionized) and organic solvents (in its acid form), non-toxic, or non-immunogenic (Lee Bs et al., Water-soluable aliphatic polyesters: poly(malic acid)s, in: Biopolymers, vol. 3a (Doi Y, Steinbuchel A eds., pp 75-103, Wiley-VCH, New York 2002, which is incorporated herein by reference as if fully set forth).

In an embodiment, a polymalic acid may be used as a molecular scaffold carrying target modules. In an embodiment, targeting modules may have functions in addition to targeting. Polymalic acid-based molecular scaffolds that may be in embodiments herein were described in PCT Appl. Nos. PCT/US04/40660, filed Dec. 3, 2004, PCT/US09/40252, filed Apr. 10, 2009, and PCT/US10/59919, filed Dec. 10, 2010, PCT/US10/62515, filed Dec. 30, 2010; and U.S. application Ser. No. 10/580,999, filed Mar. 12, 2007, issued as U.S. Pat. No. 7,935,677, and Ser. No. 12/935,110, filed Sep. 28, 2010. All of the foregoing PCT and U.S. applications are incorporated herein by reference as if fully set forth.

A polymalic acid-based molecular scaffold may be a molecule having at least two or more targeting modules attached to the polymalic acid-based molecular scaffold. The targeting modules may also transport a drug, or other therapeutic entity to a targeted tissue.

In an embodiment, the polymalic acid-based molecular scaffold may be based on poly(β-L-malic acid). The poly (β-L-malic acid) may be chemically conjugated at its carboxylic groups at defined ratios with a variety of modules.

In an embodiment, the nanoconjugate having a polymalic acid-based molecular scaffold may target cells or tissues with high specificity. The high specificity of nanoconjugates as drug vehicles may result from enhanced permeability and retention in target tissues that originates from high molecular mass, which may be greater than 20000 (Duncan R. 1999 Research Focus 2:441; Seymour L W et al., 1995 Eur J Cancer Res 31A:766).

In an embodiment, the one or more imaging moieties may include a compound suitable to facilitate an imaging procedure. The compound may be a contrast agent. An imaging may be any imaging procedure used as a clinical diagnostic tool. An imaging may be an MRI procedure that allows non-invasive imaging of optically opaque subjects and may provide contrast among soft tissues at high spatial resolution. An imaging moiety in the one or more imaging moieties may be a chelating molecule used for MRI. The chelating molecule may be but is not limited to 1,4,7,10-tetraazocyclododecane-1,4,7,10-tetraacetic acid (DOTA), dibenzo-DOTA, diethylenetriaminepentaacetic acid (DTPA), 1,4,7,10-tetraazacyclododecane-1,4,7.10-tetrakis (2-propionic acid) (DOTMA), 1,4,8,11-tetrazacyclotetradecane-1,4,8,11-tetraacetic acid (TETA), 1,4,7,-tricarboxymethyl 1,4,7,10 teraazacyclododecane triacetic acid (DO3A), 1,4,7,10-tetraazacyclo-dodecan-1-(2-hydroxypropyl)-4,7, 10-triacetic acid (HP-DO3A), ethylenediamine-tetraacetic acid (EDTA), bis-2 (hydroxybenzyl)-ethylene-diaminediacetic acid (HBED), or 1,4,7-triazacyclo-nonane N,N',N"-triacetic acid (NOTA).

In an embodiment, the chelating molecule may form a complex with a paramagnetic ion. A paramagnetic ion may be a metal ion which may magnetize parallel or antiparalell to a magnetic field. The paramagnetic ion may be a multivalent ion of paramagnetic metal. The paramagnetic metal may be selected from but is not limited to lanthanides and transition metals. The transition metals may include but are not limited to manganese, iron, chromium, nickel and cobalt. The lanthanides may include but are not limited to praseodymium, neodymium, samarium, gadolinium, terbium, dysprosium, holmium, erbium, europium and ytterbium.

In an embodiment, the contrast agent may be gadolinium, a highly paramagnetic ion. This embodiment may be utilized in an MRI procedure. Gadolinium may be combined with a chelating molecule. Gadolinium (Gd) may be combined with (2,2',2"-(2-(2-(2-mercaptoethylamino)-2-oxoethyl)-1, 4,7-tetraazacyclododecane-1,4,7-triyl)triacetic acid) (DOTA) and may form a Gd-DOTA complex. Gd-DOTA may form a stable contrast agent. Gd-DOTA may be used in humans.

A nanoconjugate herein having a high molecular weight and including a Gd-DOTA molecule may improve both the efficacy of BBB permeation and prolong the circulation time. This may improve the accumulation of the contrast agent inside brain tumor regions or in other areas with pathological conditions due to the high molecular weight of the nanoconjugate.

The one or more targeting modules attached to the polymalic acid-based molecular scaffold may include biological activities other than targeting. The one or more targeting modules may be configured to perform delivery of a prodrug. The one or more targeting modules may include a releasable functional module that may become effective in the cytoplasm. The one or more targeting modules may be configured to direct the nanoconjugate towards a specific tissue by being capable of binding to the surfaces of cells. The one or more targeting modules may be configured to facilitate internalization of the nanoconjugate into the targeted cell through endosomes. The one or more targeting modules may be configured to promote escape of the nanoconjugate from endosomes into the cytoplasm by virtue of hydrophobic functional units that integrate into and disrupt endosomal membranes. The one or more targeting modules may be configured to increase effectiveness during acidification of endosomes en route to lysosomes. The one or more targeting modules may be configured to protect against degradative enzyme activities, for example, peptidases and proteases.

In an embodiment, a targeting module may be but is not limited to an antibody, a polypeptide, an oligonucleotide, a therapeutic chemical, or a phage. The one or more targeting modules may be capable of targeting a component of a diseased cell or a tissue.

In an embodiment, a targeting module may be an antibody. The antibody may have an ability to recognize and specifically bind to a target. The target may be but is not limited to a protein, a polypeptide, a peptide, a carbohydrate, a polynucleotide, a lipid, or combinations of at least two of the foregoing through at least one antigen recognition site within the variable region of the antibody.

In an embodiment, a targeting module may be an antibody of a class described as antagonist antibodies, which specifically bind to a cancer stem cell marker protein and interfere with, for example, ligand binding, receptor dimerization, expression of a cancer stem cell marker protein, and/or downstream signaling of a cancer stem cell marker protein.

In an embodiment, a targeting module may be an antibody of a class described as agonist antibodies which specifically bind to a cancer stem cell marker protein and promote, for example, ligand binding, receptor dimerization, and/or signaling by a cancer stem cell marker protein. In an embodiment, a targeting module may be an antibody that does not interfere with or promote the biological activity of a cancer stem cell marker protein and may instead function to inhibit tumor growth by, for example, antibody internalization and/or recognition by the immune system.

A targeting module may be selected from any type of antibody. The antibody may be a polyclonal antibody, an intact monoclonal antibody, an antibody fragment, which may be but is not limited to Fab, Fab', F(ab')2, an Fv fragment, a single chain Fv (scFv) mutant, a chimeric antibody or a multispecific antibody. A multispecific antibody may be a bispecific antibody generated from at least two intact antibodies. A targeting module may be a humanized antibody or a human antibody. A targeting module may be a fusion protein comprising an antigen determination portion of an antibody. A targeting module may be fragment of an antibody comprising an antigen recognition site. Antibodies selected from may include any of the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu. A targeting module may be a naked antibody or an antibody conjugated to other molecules. A targeting module may be an antibody conjugated to, for example, toxins or radioisotopes.

In an embodiment, a targeting module may be a monoclonal antibody. In an embodiment, a targeting module may be a polyclonal antibody. In an embodiment, a targeting module may be an antibody specific to at least one vasculature protein in a cell. The vasculature protein may be a transferrin receptor protein. The transferrin receptor protein as used herein refers to the receptor expressed on endothelium cell surfaces, and at elevated levels on certain tumors (Lee J H et al. 2001 Eur J Biochem 268:2004; Kovar M K et al., 2003 J Drug Targeting 10:23). A monoclonal antibody targeting module (TfR-mAb) may bind the transferrin receptor protein and thereby achieve transcytosis through endothelium associated with BBB. An embodiment includes Tfr-mAb attached to a Gd-containing nanoconjugate that may bind specifically to transferrin receptor residing at the endothelial surface on the luminal side of brain capillaries thus binding the nanoconjugate thereto. Once bound, the nanoconjugate may efficiently cross the BBB endothelium by transcytosis. A Tfr mAb-containing nanoconjugate may be of the size of 20-30 nm (molecular weight 100,000), which is known to be well above the renal exclusion limit.

A TfR mAb targeting module may be a humanized (hu-Tfr-mA) or a chimeric antibody. To study in vivo imaging in mouse and rat models of Alzheimer's disease (AD models), or TNBC metastasized to brain, hu-TfR mAb of the nanoconjugate could be replaced by mouse- or rat-TfR mAb. The nanoconjugate may contain other polypeptides used for similar purposes.

A targeting module may include a lectin or another ligand specific to the transferrin receptor. A targeting module may be a ligand to one of any number of cell surface receptors or antigens.

A targeting module may be a small drug molecule or a chromophore molecule, or a protein molecule, or a lectin that are covalently joined to polymalic acid in constructing the nanoconjugate.

A targeting module may be an antibody configured to specifically bind a protein selected from but not limited to EGFR, human epidermal growth factor (HER), laminin 411, insulin-like growth factor (IGF) and tumor necrosis factor-alpha (TNF-α). The antibody binding EGFR may be Cetuximab. The antibody binding HER may be Herceptin®. The antibody binding laminin 411 may bind either laminin β1 subunit, or laminin α4 subunit, or both.

A targeting module may be an oligonucleotide. The oligonucleotide may be an antisense oligonucleotide inhibiting expression of a target nucleic acid molecule. The oligonucleotide may be one of the antisense oligonucleotides inhibiting expression of lamin 411 that were described in PCT Appl. PCT/US04/29956, filed Sep. 13, 2004; and U.S. application Ser. No. 10/570,747, filed Jan. 30, 2007, issued as U.S. Pat. No. 7,547,511, and Ser. No. 12/473,992, filed May 28, 2009, which are incorporated by reference as if fully set forth.

A targeting module may include an endosomal escape unit as described in PCT application PCT/US09/40252, filed Apr. 10, 2009, which is incorporated by reference as if fully set forth. An endosomal escape may be a carrier module attached to the polymalic acid-based scaffold that becomes active by acidification during maturation of the endosomal vesicles towards lysosomes. The carrier module may include a plurality of leucine residues in a polypeptide linked to the polymalic acid-based molecular scaffold by amide bonds. The carrier module may include a plurality of valine residues in a polypeptide linked to the polymalic acid-based molecular scaffold by amide bonds. The carrier module may include a leucine ethylester linked to the polymalic acid-based molecular scaffold by amide bonds. During acidification of the endosomes en route to lysosomes, these stretches of the carrier module may become charge-neutralized and hydrophobic, and capable of disrupting membranes. Other molecules that become charge neutralized at lysomal pH's may be used in place of leucine or valine residues, or a leucine ethylester in construction of the compositions containing polymalic acid and an endosomal escape unit module.

A targeting module may be a module for protection against resorption by the reticuloendothelial system (RES) and/or enzyme degradation. For example, the module for protection against resorption may be but is not limited to a polyethylene glycol (PEG) molecule. PEG may be used to increase the in vivo half-life of conjugated proteins, to prolong the circulation time, and enhance extravasation into targeted solid tumors (Arpicco S et al. 2002 Bioconjugate Chem 13:757; Maruyama K et al., 1997 FEBS Letters 413:1771, which is incorporated by reference as it fully set forth). Other molecules known to increase half-life of the nanoconjugate may be used in design of nanoconjugates herein.

FIG. 1 depicts an exemplary nanoconjugate including Gd-DOTA complex attached to the polymalic acid platform. The nanoconjugate may be for tumor-type specific MRI in mouse model for human TNBC metastasized to brain. The modules attached to the polymalic acid may include an MRI contrast agent (Gd-DOTA), targeting modules (chimeric mouse-human monoclonal antibodies Cetuximab (Erbitux®) specific to EGFR displayed by tumor cells and MsTfR for penetration through BBB) and a carboxyl group for improving solubility. For use in humans, the anti-mouse TfR mAb may be replaced by anti-human TfR mAb.

Polymalic acid of any molecular weight (Mw) may be used as the platform to carry one or more targeting modules and one or more imaging moieties. Polymalic acid used herein may have a Mw of 10,000; 15,000; 20,000; 30,000; 40,000; 50,000; 60,000; 70,000; 80,000; 90,000; 100,000; 110,000; 120,000; 130,000; 140,000; or 150,000, or more, or any value in a range between any two of the foregoing (endpoints inclusive). The polymalic acid of Mw 80,000 may be platform for a nanoconjugate that caries covalently bound MsTfR mAb and a tumor specific mAb together with multiple covalently bound Gd-DOTA. The platform may contain any number of derivatisable carboxyl group. In embodiments, the platform may contain 700 or more derivatisable carboxyl groups and a large number of Gd-DOTA units can be loaded for generating a strong MRI signal.

In an embodiment, one or more targeting modules may be capable of targeting a component of a diseased cell or tissue. The component may be, but not limited to, beta amyloid plaques thought to contribute to the degradation of the neurons in the brain and the subsequent symptoms of Alzheimer's disease. The one one or more targeting modules may include curcumin (5-hydroxy-1,7-bis(4-hydroxy-3-methoxyphenyl)-1,4,6-heptatrien-3-on) for specific binding to Alzheimer's amyloid plaques. Curcumin may bind specifically and tightly to the beta amyloid plaques and thereby may allow accumulation of the nanoconjugate within the brain and a high staining intensity. The nanoconjugate may contain one or more curcumin molecules. The presence of multiple curcumin molecules on the nanoconjugate results in firm attachment of the nanoconjugates around to a beta-amyloid plaque contributing to sharp contours with high contrast.

The nanoconjugate molecule containing curcumin may carry any number of gadolinium ions. The nanoconjugate may carry a single gadolinium ion. The nanoconjugate may carry a plurality of gadolinium ions. The nanoconjugate may carry 1, 5, 10, 20, 30, 40, 50, 60, or more Gd ions per molecule of nanoconjugate. The nanoconjugate may carry a number of Gd ions per molecule of nanoconjugate in a range between any two of the following numbers: 1, 5, 10, 20, 30, 40, 50, or 60. A high concentration of Gd on a target tissue, for example amyloid plaques, may allow imaging by MRI at high contrast and resolution quality.

The one or more targeting module may include therapeutic polypeptides. In embodiments, the one or more targeting modules may include additional therapeutic agents. In embodiments, the additional therapeutic agent or agents is selected from the group consisting of growth factors, anti-inflammatory agents, vasopressor agents, collagenase inhibitors, topical steroids, matrix metalloproteinase inhibitors, ascorbates, angiotensin II, angiotensin III, calreticulin, tetracyclines, fibronectin, collagen, thrombospondin, transforming growth factors (TGF), keratinocyte growth factor (KGF), fibroblast growth factor (FGF), insulin-like growth factors (IGF), epidermal growth factor (EGF), platelet derived growth factor (PDGF), neu differentiation factor (NDF), hepatocyte growth factor (HGF), and hyaluronic acid.

In an embodiment, the nanoconjugate may include a tracking fluorescent dye to follow in vivo distribution of the nanoconjugate in a subject. The tracking dye may facilitate gross in vivo monitoring of the nanoconjugate distribution by imaging systems other than by using MRI. In the absence of Gd, the tracking dye may allow the validation of curcumin-polymalic acid conjugate entrance into the brain in the first phase of the investigation of a disease or condition in a subject. A tracking dye may also validate whether curcumin is attached to polymalic acid within the brain. Thus, the tracking dye may be useful in optimization experiments. Tracking may be performed, for example, by using Xenogen fluorescence imaging system.

In an embodiment, a kit for facilitating imaging of a cell or tissue is provided. The cell may be a diseased cell. The tissue may be a diseased tissue. The kit may be implemented in a method for visualizing pathological conditions. The kit may include a nanoconjugate comprising a polymalic acid-based molecular scaffold, one or more imaging moiety and one or more targeting module. The kit may include any one or more nanoconjugates described herein. At least one of the imaging moieties and at least one of the targeting modules may be conjugated to the polymalic acid-based molecular scaffold. All of the imaging moieties may be conjugated to the polymalic acid-based molecular scaffold. All of the targeting modules may be conjugated to the polymalic acid-based molecular scaffold.

The exact nature of the modules and moieties configured in the kit may depend on its intended purpose. In embodiments, the kit may be configured for the purpose of visualizing, treating or monitoring Alzheimer's disease or other conditions involving abnormal brain function, activity or pathology. For this purpose, the kit may include a nanoconjugate comprising a module for binding amyloid beta plaque and MRI imaging. In embodiments, the kit may be configured for the purpose of visualizing, treating, or monitoring cancer.

In an embodiment, the kit may be configured particularly for the purpose of treating mammalian subjects. The kit may be configured particularly for the purpose of treating human subjects. The kit may be configured for veterinary applications. The kit may be configured to, but is not limited to, treating farm animals, domestic animals, or laboratory animals. Instructions for use may be included in the kit. Instructions for use may include a tangible expression describing the technique to be employed in using the components of the kit to effect a desired outcome. For example, instructions may describe the technique to visualize amyloid beta plaques or tumor cells or cell types. The kit may also contain other useful components. For example, the kit may contain diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit may be provided to the practitioner stored in any convenient and suitable ways that preserve their operability and utility. For example, the components may be provided be in dissolved, dehydrated, or lyophilized form. The components may be provided at room, refrigerated or frozen temperatures. The components may be contained in suitable packaging material(s). As used herein, the phrase "packaging material" refers to one or more physical structures used to house the contents of the kit, such as inventive compositions and the like. The packaging material may be constructed by well known methods, preferably to provide a sterile, contaminant-free environment. As used herein, the term "package" refers to a suitable solid matrix or material such as glass, plastic, paper, foil, and the like, capable of holding the individual kit components. The packaging material may have an external label which indicates the contents and/or purpose of the kit and/or its components.

In an embodiment, a method of targeting a cell or a tissue in a subject is provided. The cell may be a diseased cell. The tissue may be a diseased tissue. The method may involve administering to the subject a nanoconjugate that includes a polymalic acid-based molecular scaffold, at least one imaging moiety, and at least one targeting module. At least one of the imaging moieties and the at least one of the targeting modules may be conjugated to the polymalic acid-based molecular scaffold. All imaging moieties may be conjugated to the polymalic acid-based molecular scaffold. All targeting modules may be conjugated to the polymalic acid-based molecular scaffold. The nanoconjugate may be any nanoconjugate described herein. The method may also include providing conditions permitting interaction of the nanoconjugate with a component of the diseased cell or a diseased tissue.

The subject may be a patient. As used herein, the term "patient" refers to a human. The patient may be a human with a symptom or symptoms of a disease or condition. The patient may need treatment for the disease or condition in a clinical setting. The symptoms of the disease or condition may change as a result of a treatment, or spontaneous remission, or development of further symptoms with the progression of the disease. The term "patient" may also refer to non-human organism. The patient may be a laboratory animal, a farm animal or a zoo animal. The patient may be a mouse, a rat, a guinea pig, a hamster, a horse, a rabbit, a goat, or a cow.

In an embodiment of the method of targeting a cell or a tissue, a nanoconjugate may be administered to a subject by any suitable route. The nanoconjugated may be administered by intravenous injections. The nanoconjugate may be delivered by a technique selected from the group consisting of: intramuscular injection, subcutaneous injection, intravenous injection, intradermal injection, intranasal injection, inhalation, oral administration, sublingual administration, buccal administration, or topical administration.

In an embodiment of the method of targeting a cell or a tissue, the at least one imaging moiety may be a molecule facilitating an imaging technique. An imaging may be performed by any technique including but not limited to X-ray imaging, computer tomography (CT) scans, and MRI. The imaging moiety may include an imaging contrast agent. The imaging contrast agent may be a Gd-DOTA. The method may involve visualizing the imaging contrast agent in the subject. Visualizing may be performed by the imaging technique; e.g., by X-ray, CT, or MRI.

In an embodiment, the method of targeting a cell or a tissue may also include diagnosing a disease or other condition in the subject. Diagnosing may be based on an image of the diseased cell or the diseased tissue. Diagnosing may include comparing the image with a control image of a normal cell or tissue in a healthy individual. The image may be obtained by any non-invasive clinical diagnostic imaging procedure. For example, the image may be obtained by MRI. The MRI apparatus utilizes the nuclear magnetic resonance phenomenon and may produce images of cross sections of the cells or tissues being imaged. The MRI may measure signal derived from protons of the water molecules present in cells or tissues in a subject positioned for imaging. The intensity of MRI images may depend on physical properties of specific tissues. The intensity of MRI signal may depend on proton density, spin lattice relaxation time (T1), and the spin-spin relaxation time (T2).

An "abnormal condition" refers to a function in the cells and tissues in a body of a patient that deviates from the normal function in the body. An abnormal condition may refer to a disease. Abnormal condition may include brain disorders. Brain disorders may be but are not limited to Alzheimer's disease, Multiple sclerosis, Parkinson's disease, Huntington's disease, schizophrenia, anxiety, dementia, mental retardation, and anxiety. Abnormal condition may include proliferative disorders. The terms "proliferative disorder" and "proliferative disease" refer to disorders associated with abnormal cell proliferation. Proliferative disorders may be, but are not limited to, cancer, vasculogenesis, psoriasis, and fibrotic disorders. Cancer is a physiological condition in mammals in which a population of cells is characterized by unregulated cell growth. Examples of cancers include, but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancers. Breast cancer may include TNBC and HER2-positive breast cancer.

Cancer may be a primary cancer or a metastatic cancer. The term "primary cancer" refers to the original site at which a cancer originates. For example, a cancer originating in the breast is called a primary breast cancer. If it metastasizes; i.e., spreads to the brain, the cancer is referred to as a primary breast cancer metastatic to the brain.

The term "metastasis" refers to the process by which a cancer spreads or transfers from the site of origin to other regions of the body with the development of a similar cancerous lesion; i.e., having the same or substantially the same biochemical markers at the new location. A "metastatic" or "metastasizing" cell is one that has a reduced activity for adhesive contacts with neighboring cells and migrates by the bloodstream or within lymph from the primary site of disease to additional distal sites, for example, to invade neighboring body structures or distal structures.

An abnormal condition may also include diabetes, rheumatoid arthritis, asthma, psoriasis, atherosclerosis, cardiovascular disorders, glaucoma, and retinopathy. The term "disease" refers to all abnormal conditions. Diagnosing may include diagnosing of another condition in addition to an abnormal condition. The other condition may be associated with an abnormal condition. The other condition may not be associated with an abnormal condition. For example, diagnosing of schizophrenia may be made in addition to diagnosing Alzheimer's disease.

The term "tumor" refers to any mass of tissue that result from excessive cell growth or proliferation, either benign (noncancerous) or malignant (cancerous) including pre-cancerous lesions. Tumor cell may derive from a tumor or a pre-cancerous lesion including both a non-tumorigenic cell and a tumorigenic cell; i.e., cancer stem cell.

An embodiment includes a tumor-specific nanoconjugate, which may be implemented for enhancement of MRI and facilitating diagnostic imaging. An enhancement includes such a method. In particular, a tumor-specific nanocomjugate may be used to distinguish between tumor and non-tumor lesions of the brain which are indistinguishable by a common MRI procedure. A nanoconjugate may be used to distinguish between different types of tumors occurring side-by side in the same individual. A nanoconjugate may be used for MRI enhancement in the brain of cancer patient with a history of primary breast cancer, metastatic brain tumor from primary breast cancer, metastatic tumors from a different type of cancer, a primary brain tumor, and/or infection resulting from impairment of the immune system as a complication of chemotherapy.

A nanoconjugate herein may be designed to enhance MRI-based diagnostics of specific conditions. In an embodiment, a nanoconjugate (MRI enhancer) may include antibodies specific for tumor markers at the surface of tumor cells. The antibodies may be specific to overexpressed cell-surface antigens such as EGFR, HER2, B lymphocyte antigen CD 20 or laminin. The antibodies may facilitate access to the tumor tissue across the BBB into tumor interstitial using transcytosis through targeting of transferrin receptor on the endothelium of tumor capillaries. Once attached, the enhancer could be retained over a time scale that exceeds by far the clearance of unbound free MRI enhancer through the kidneys. On basis of the prolonged retention in the brain or other tumors, MRI could recognize the labeled tumor by a signal sent as a shortened relaxation time T1 of the reagent surrounding water molecules after given pulses of a spin orientating external magnetic field of the MRI apparatus. The shortening of the reciprocal of T1 is proportional to the concentration of the MRI enhancer, and thus the enhancement of the signal may be the result of an accumulation due to tumor specific binding. The tumor nonspecific MRI signal may be accounted for by measurement of T1 measured for healthy portions of the brain. The difference of T1 values between tumor and healthy brain may be measured as a function of time reflecting specific tumor retention of the enhancer reagent, while the reagent in the healthy brain and elsewhere may be already cleared through the kidneys. Tumor-type specific MRI scanning may be performed when T1 for the healthy brain has approached zero value.

A number of contrast agents may be included in a nanoconjugate herein to improve resolution of MR images. A contrast agent may be a molecule suitable to generate a contrasting effect in vivo. A contrast agent may form metalloprotein complex. A contrast agent may form a complex that affects the relaxation times T1, or T2, or both. A contrast agent that affects T1 may be a lanthanide metal ion. A contrast agent may be Gd that is chelated to a low molecular-weight molecule in order to limit toxicity. A contrast agent that affects T2 may consist of small particles of magnetite (FeO—$Fe_2O_3$). Contrast agents may interact with mobile water in tissue to produce contrast.

In an embodiment, diagnosing the disease or condition may involve a patient with abnormal brain function, activity or pathology. Diagnosing the Alzheimer disease may be based on the presence of amyloid beta plaques in the patient's brain.

Diagnosing may be performed by administering a composition that includes a polymalic-acid based nanoconjugate containing a targeting module for binding amyloid beta plaques and an imaging moiety for MRI imaging to the patient and acquiring images of localization of the nanoconjugate in a particular type of tissue in the patient's body.

The nanoconjugate may be able to pass the BBB and then target plaques, a hallmark of Alzheimer's disease, by simultaneously having attached plaque-binding curcumin and TfR mAb. Access to beta-amyloid plaque imaging may allow determining the status of Alzheimer's disease and to follow patients during the treating the disease. Similar Polycefin nanoconjugates containing curcumin and/or other active compounds could be used to treat Alzheimer's disease.

In an embodiment, application of a nanoconjugate may improve both the efficacy of BBB permeation and may prolong circulation of the Gd-containing contrast agent. It may also improve the accumulation inside brain regions that contain plaques due to tight binding to Alzheimer's amyloid plaques to curcumin.

In an embodiment, targeting the diseased cell or tissue may result in reduction or elimination of at least one symptom of the disease or condition, and thereby treatment of the disease or condition in the subject. Targeting the diseased cell or tissue may be a therapeutic measure to promote regression of a cancer or prevent further development or metastasis, or as a prophylactic measure to minimize complications associated with development of a tumor or cancer.

In an embodiment, the condition and/or disease monitored or treated may be Alzheimer's disease. In an embodiment, a method of treating a condition in a patient is provided. The method may include administering a composition comprising a nanoconjugate comprising a targeting module for binding amyloid beta plaques and an imaging moiety for MRI imaging. The method may also include treating the patient with the composition.

To achieve the desired effect; i.e., inhibit the expression of at least one ligand of the target receptor, a composition may be administered at a therapeutically effective amount. A "therapeutically effective amount" of the composition may be the amount effective for preventing further development of a cancer or transformed growth, and even to effect regression of the cancer.

The exact dosage may be chosen by the individual physician with regard to the need of the patient to be treated. Dosage and administration may be adjusted to provide sufficient levels of the active agent(s) or to maintain the desired effect. Additional factors which may be taken into account include the severity of the disease state; e.g., cancer size and location; age, weight and gender of the patient; diet, time and frequency of administration; drug combinations; reaction sensitivities; and tolerance/response to therapy. Long acting compositions might be administered every 3 to 4 days, every week, or once every two weeks depending on half-life and clearance rate of the particular composition.

In an embodiment, the one or more targeting modules may include active agents for treating a disease or condition in a patient. The active agents may be formulated in dosage unit form for ease of administration and uniformity of dosage. The expression "dosage unit form" as used herein refers to a physically discrete unit of active agent appropriate for the patient to be treated.

For any active agent, the therapeutically effective dose may be estimated initially either in cell culture assays or in animal models, usually mice, rabbits, dogs, or pigs as shown in Examples herein. The animal model may be also used to achieve a desirable concentration range and route of administration. Such information may then be used to determine useful doses and routes for administration in humans. A therapeutically effective dose refers to that amount of active agent which ameliorates the symptoms or condition. Therapeutic efficacy and toxicity of active agents can be determined by standard pharmaceutical procedures in cell cultures or experimental animals, e.g., ED50 (the dose is therapeutically effective in 50% of the population) and LD50 (the dose is lethal to 50% of the population). The dose ratio of toxic to therapeutic effects is the therapeutic index, and it can be expressed as the ratio, LD50/ED50. Compositions herein may exhibit large therapeutic indices. The data obtained from the animal studies may be used in formulating a range of dosage for human use.

As discussed above and described in greater detail in the Examples, a nanoconjugate herein may be administered in a method to prevent development or metastasis of a cancer condition. In particular, a nanoconjugate may be useful in preventing further growth of a particular cancer type, including but not limited to breast cancer; skin cancer; ovarian cancer; cervical cancer; retinoblastoma; colon cancer and other conditions including those arising from the lining of the gastrointestinal tract; lung cancer and cancers of the respiratory tract; renal carcinoma and other tumors arising from the inner surface of kidney tubules; leukemias and lymphomas and such disorder of blood; and other types of genital cancer including those associated with various strains of papilloma virus; brain tumors; and cancers of the uterus, of the vagina, and of the urethra.

In embodiments, diagnostic, prognostic and therapeutic methods may not be limited to treating conditions in humans, but may involve similar conditions in any mammal including but not limited to bovine, canine, feline, caprine, ovine, porcine, murine, and equine species.

In an embodiment, a method of monitoring an efficiency of treatment of a disease or condition in a subject is provided. Monitoring may include obtaining a first image of a diseased cell or a diseased tissue in the subject after treatment, and, after a period of time, a second image of the diseased cell or tissue. Comparison can be made between the first and the second images to determine a clinically significant difference in cells and tissues after the treatment. For example, two or more images may be compared to determine whether the treatment reduced the number of cancer cells in a tumor, or the size of a particular tumor.

A subject may be a patient in need of MRI procedure. A composition that includes a polymalic acid-based molecular scaffold, at least one imaging moiety, and at least one targeting module may be administered at any time before or after placing a patient in an MRI apparatus. The composition may target cells or tissues at different locations of the patient's body before images may be produced. In this case, the composition may be accumulated in the specific location before imaging. The images may be also produced during the period of accumulation of the composition in target cells or tissues. Any disease cells or tissues targeted by the composition may be identified by examining the image or images. The composition may be re-administered to the subject after a period of time depending on the scheme of a particular therapeutic treatment. For example, the composition may be administered every week, every two weeks, every three weeks, or every month. Image(s) may be produced during or after subsequent administration of the composition and comparison may be made between images taken during different phases of therapeutic treatment to assess the efficacy of treatment.

Methods herein may include providing a period of time sufficient for accumulation of a nanoconjugate in targeted cells or tissues.

In another embodiment, a method of prognosing a condition and/or disease is provided for an individual having abnormal brain function, activity or pathology. The method may include administering a composition comprising a nanoconjugate comprising a targeting module for binding amyloid beta plaques and a module for MRI imaging to the individual, and prognosing a severe form of the condition and/or disease based on the presence of an extensive level of amyloid beta plaques in the individual relative to a normal subject.

In an embodiment, a composition including a polymalic acid-based molecular scaffold, at least one imaging moiety, and at least one targeting module may further include a pharmaceutically acceptable carrier. As used herein, the term "pharmaceutically acceptable carrier" includes any and all solvents, diluents, or other liquid vehicle, dispersion or suspension aids, surface active agents, isotonic agents, thickening or emulsifying agents, preservatives, solid binders, and lubricants as suited to the particular dosage form desired. A pharmaceuitically acceptable carrier may be one described in *Remington's Pharmaceutical Sciences* Ed. by Gennaro, Mack Publishing, Easton, Pa., 1995, which is incorporated herein by reference as it fully set forth, and discloses various carriers used in formulating pharmaceutical compositions and known techniques for the preparation thereof. Some examples of materials which can serve as pharmaceutically acceptable carriers include but are not limited to sugars, lactose, glucose, and sucrose; starches, corn starch and potato starch; cellulose and its derivatives, sodium carboxymethyl cellulose, ethyl cellulose, and cellulose acetate; powdered tragacanth; malt; gelatin; talc; excipients, cocoa butter and suppository waxes; oils, peanut oil, cottonseed oil, safflower oil, sesame oil, olive oil, corn oil, and soybean oil; glycols, propylene glycol; esters,ethyl oleate and ethyl laurate; agar; buffering agents, magnesium hydroxide, and aluminum hydroxide; alginic acid; pyrogen-free water; isotonic saline; Ringer's solution; ethyl alcohol, and phosphate buffer solutions, as well as other non-toxic compatible lubricants, sodium lauryl sulfate and magnesium stearate. Coloring agents, releasing agents, coating agents, sweetening, flavoring and perfuming agents, preservatives and antioxidants may also be present in the composition.

In an embodiment, a method of synthesizing a nanoconjugate is provided. The method may include providing a polymalic acid having a plurality of pendant carboxyl groups. The method may include reacting a compound containing sulfhydryl groups and amino groups through the pendant carboxyl group to add sulfhydryl groups to the polymalic acid to form an activated polymalic acid. The method may also include reacting at least one imaging moiety containing a sulfhydryl binding group to the activated polymalic acid to form a preconjugate. The method may further include reacting at least one targeting module containing a sulfhydryl binding group to the activated polymalic acid.

The method of synthesizing may include activating pendant carboxyl carboxyl groups on polymalic acid by adding N-hydroxysuccinimide (NHS) to the polymalic acid to form an NHS-ester. The method may also include reacting the activated carboxyl groups with the amino group of 2-mercapto-ethane-1-amine. The method may also include reacting at least one imaging moiety containing an amino group with the NHS-activated pendant carboxyl group. The method also may involve reacting at least one targeting module containing a sulfhydryl group to the preconjugate. The at least one imaging moiety may include an activated molecule of a contrast agent. The activated molecule of the contrast agent may include gadolinium (Gd)-1,4,7,10-tetraazocyclododecane-1,4,7,10-tetraacetic acid (DOTA)-amine. The at least one targeting module may include an activated antibody. The activated antibody may include an antibody-polyethylene glycol-maleimide. The antibody-polyethylene glycol-maleimide may further react with the preconjugate to form the nanoconjugate.

The at least one targeting module may include an activated curcumin-polyethylene-glycol amine. The at least one targeting module may specifically bind to a component of a diseased cell or tissue in a subject selected from the group consisting of: an epidermal growth factor receptor (EGFR), human receptor growth factor (HER), laminin 411, insulin-like growth factor (IGF), transferrin receptor protein, curcumin and tumor necrosis factor-alpha (TNF-$\alpha$).

A polymalic acid having one or more targeting modules may be synthesized by any known method. For example, a polymalic having attached one or more target modules may be synthesized by ring-opening polymerization of derivatized malic acid lactones. Doxorubicin-poly-malic acid may be synthesized from synthetic poly-$\beta$-D, L-malic acid.

Further embodiments herein may be formed by supplementing an embodiment with one or more element from any one or more other embodiment herein, and/or substituting one or more element from one embodiment with one or more element from one or more other embodiment herein.

EXAMPLES

The following non-limiting examples are provided to illustrate particular embodiments. The embodiments throughout may be supplemented with one or more detail from one or more example below, and/or one or more element from an embodiment may be substituted with one or more detail from one or more example below.

Example 1. Chemical Synthesis of a Tissue Specific Nanoconjugate for MRI Enhancement Materials.

High purity polymalic acid (PMLA; Mw 800,000, polydispersity factor P=1.2 by Sec-HPLC) isolated from the culture medium of *Physarum polycephalum* was used as Polycefin platform (Ljubimova J Y et al. 2007 Chem-Biol Interactions 171:195). Mouse anti-human TfR mAb RVS10 was purchased from Southern Biotech (Birmingham, Ala., USA) and ERBITUX® (Cetuximab) from Bristol-Myers Squibb (New York, N.Y., USA). mPEG$_{5000}$-Amine and maleimide-PEG$_{3400}$-maleimide were obtained from Laysan Bio, Inc. (Arab, Ala., USA). 3-(2-Pyridyldithio)-propionate (PDP; Carlsson J et al. 1978 Biochem J 173:723. Alexa Fluor® 680 C2 maleimide (Alex680) was purchased from Invitrogen Corporation (Carlsbad, Calif., USA), 2-Amino-ethyl-mono-amide-DOTA-tris(t-Bu ester) from (Macrocyclics, Inc. TX, USA). Unless indicated, chemicals and solvents of highest purity were obtained from Sigma-Aldrich (St. Louis, Mo.) USA.

Analytical Methods for Chemical Synthesis.

The conjugation reaction of Gd-DOTA-amine and 2-MEA with PMLA was followed by thin layer chromatography (TLC) on precoated silica gel 60 F254 aluminum sheets (Merck, Darmstadt, Germany) under UV light and/or by ninhydrin staining. Size exclusion chromatography was performed on an Elite LaChrom analytical system with Diode Array Detector L 2455 (Hitachi, Pleasanton, Calif., USA), and $M_w$, was measured using either BioSep-SEC-S 3000 or PolySep-GFC P4000 (300×7.80 mm; Phenomenex, Torrance, Calif., USA) using 50 mM sodium phosphate buffer pH 6.8 as mobile phase (0.75 mL/min) and polystyrene sulfonates as molecular weight standards. Thiol residues were assayed by the method of Ellman (Ellman G L 1959 Arch Biochem Biophys 82:70). TfR binding activity of anti-mouse TfR mAb conjugated to polymalic acid was assayed using Protein Detector™ ELISA Kit (KPL, Inc., Gaithersburg, Mass., USA). The mouse TfR ectodomain used as the antigen was obtained from Protein Expression Center, California Institute of Technology (Pasadena, Calif. USA). Binding of polymalic acid conjugated Cetuximab to EGFR expressed on triple-negative breast cancer cells was demonstrated by fluorescence activated cell sorting (FACS) analysis. Gadolinium was measured by ICP-MS at UCLA, Los Angeles, Calif., USA). In the absence of protein, the reaction of DOTA-Gd was followed by its intrinsic fluorescence at 280 nm excitation wavelength and 316 nm emission wave length (Hagan J J et al. 1988 Anal Biochem. 60:514).

Example 2. Synthesis—an Overview

Figure 2:
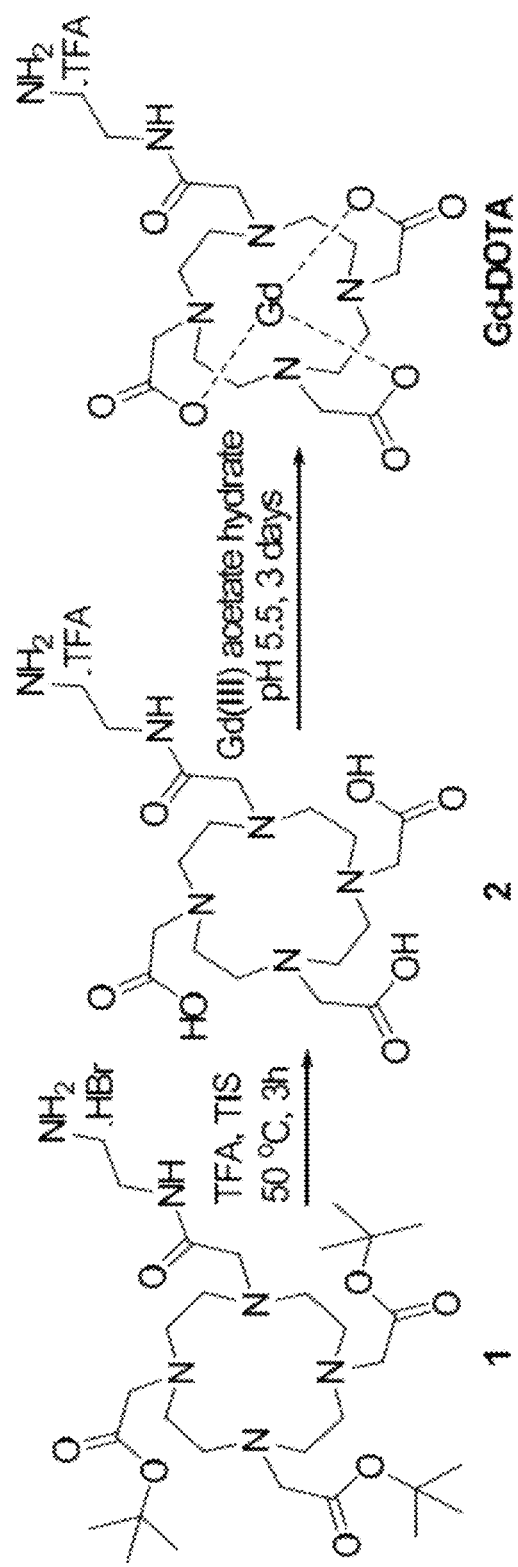
FIG. 2 is a diagram illustrating synthesis of gadolinium (Gd)-1,4,7,10-tetraazocyclododecane-1,4,7,10-tetraacetic acid (DOTA) amine.
Figure 3:
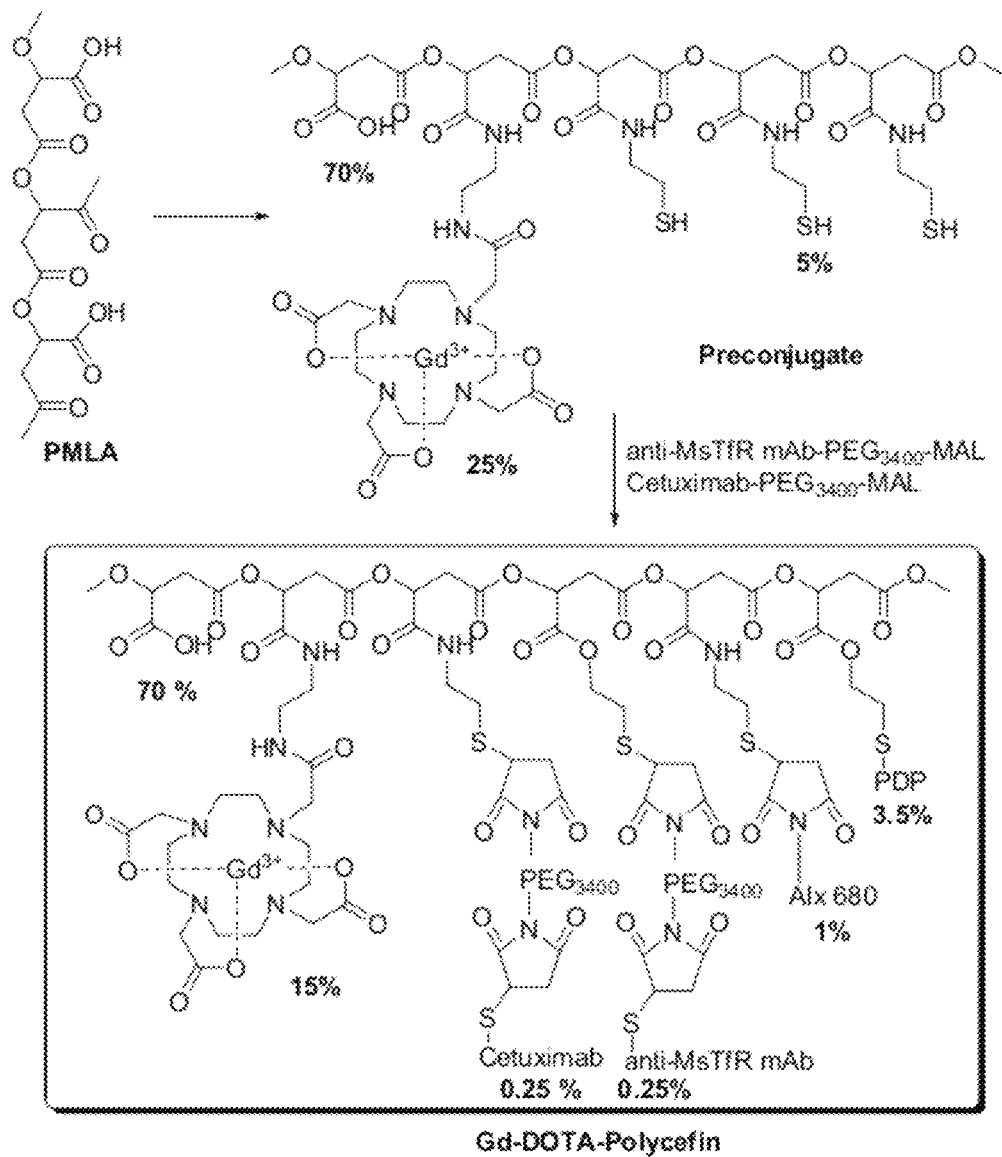
FIG. 3 is a diagram illustrating synthesis of the Gd-DOTA-Polycefin nanoconjugate.

Synthesis of the tumor-type specific MRI enhancer reagent was accomplished in two parts: first the synthesis of Gd-DOTA-amine (FIG. 2) and second the conjugation of Gd-DOTA-amine to NHS-activated PMLA (FIG. 3). The alternative route includes first conjugating DOTA-amine with PMLA and then loading with $Gd^{3+}$. The first part of the synthesis started with deprotection of the commercially available DOTA amino derivative (FIG. 2). The conjugation of Gd-DOTA amino with activated polymalic acid shown in FIG. 3 may be subject to variation for further increase in number of Gadolinium per polymer chain and for increase in reaction yields.

Example 3. General Procedure for Boc Deprotection

Referring to FIG. 2, (1) 2-Aminoethyl-mono-amide-DOTA-tris(t-Bu ester) (1.23 g, 1.77 mmol) was dissolved in trifluoroacetic acid (TFA) (25 mL) and Triisopropylsilane (TIS) (1.12 g, 7.1 mmol) was added. The reaction mixture was stirred at 50° C. for 3 hours and cooled to room temperature. Evaporation of the solvent under reduced pressure yielded viscous brown oil. An ice-cold diethyl ether (25 mL) was added and the white precipitate was filtered and washed with diethyl ether. The dried precipitate was dissolved in pure water and freeze dried. Reaction yield was 97%.

Example 4. General Procedure for Preparation of Metal Complex

Referring to FIG. 2, an equivalent of DOTA amine (2) (295 mg, 0.56 mmol) dissolved in 4 mL of water, received dropwise a slight stoichiometric excess of a Gadolinium (III) acetate (250 mg, 0.61 mmol) in 4 mL of water. The solution was stirred at room temperature (RT) while the pH was continuously maintained at pH 5.5 by adding 1M KOH. After stirring for 48 hours, EDTA (0.2 equivalent) was added and the mixture stirred at room temperature for 1 hour and then freeze dried. Reaction yield was 95%.

Example 5. Synthesis of Preconjugate [P/Gd-DOTA(15%)/MEA(5%)]

N-Hydroxysuccinimide (NHS) (0.62 mmol) and N,N'-dicyclohexylcarbodiimide (DCC; 1 mmol) dissolved in 2 mL of dimethylformamide (DMF) were added consecutively to 72 mg of PMLA (0.62 mmol with regard to malyl units) in 1.5 mL of anhydrous acetone. After stirring at RT for 3 hours to complete the activation the mixture was filtered and acetone removed by rotary evaporation. A solution of Gd-DOTA in DMF 15 Mol-% (with regard to malyl units) was added drop-wise at RT under stirring followed by addition of 0.15 mmol of triethylamine (TEA). The reaction was complete after 2 h according to TLC (ninhydrin, Rf=0 for the polymer conjugate, Rf=0.2 for Gd-DOTA; n-butanol:acetic acid:water 1:1:1). After addition of 2-mercapto-ethane-1-amine (MEA) 0.5 mmol of in DMF (100 µL, 5 Mol-% with regard to malyl units) and stirring at RT for 1 hour, buffer (100 mM sodium phosphate and 150 NaCl, pH 6.8) was added and stirring continued at RT for 30 min. After centrifugation at 1500×g for 10 minutes the clear supernatant was passed over a Sephadex column (PD-10, GE Healthcare, Piscataway, N.J., USA) equilibrated with deionized (DI) water. The product containing fractions containing the conjugate polymalic acid (P), Gd-DOTA(15%) and 2-mercapto-ethane-1-amine (MEA; 5%) were lyophilized (white powder). Reaction yield was 34.4%.

Referring to FIG. 3, the PMLA based preconjugate contains 25% of Gd-DOTA, 70% of derivatisable carboxyl groups and 5% of sulfhydryl groups.

Example 6. General Procedure for Synthesis of Antibody-$PEG_{3400}$-Maleimide

Referring to FIG. 3, antibodies (each of anti-MsTfR mAb and Cetuximab; 5 mg~33 nmol, Mr~150 kD) were dissolved in 2 mL of 100 mM sodium phosphate buffer containing 150 mM NaCl pH 5.5. Tris(2-carboxy ethyl) phosphine hydrochloride (TCEP, 50 mM in water) was added at a final concentration of 5 mM. After 30 minutes at room temperature. TCEP was removed over Sephadex PD10 and the reduced antibody was immediately added dropwise to maleimide (MAL)-$PEG_{3400}$-MAL (10 mmol) dissolved in 5 mL sterile sodium phosphate buffer, 100 mM, 150 mM NaCl(pH 5.5) (always freshly prepared before use). After overnight stirring at 4° C., the mixture was concentrated over centrifuge membrane filter (Vivascience, cut off 30 kD, 20 mL, 100 mM sodium phosphate buffer containing 150 mM NaCl, ~pH 5.5) and purified over Sephadex G75 equilibrated with 100 mM sodium phosphate buffer, 150 mM NaCl, pH 6.2. Reaction yield was 75-85%

Example 7. General Procedure for Synthesis a Gd-DOTA-Polycefin Nanoconjugate

A total of 6 mg (2 mg/mL) of anti-mouse transferrin receptor mAb (anti-MsTfR mAb) and Cetuximab (each conjugated with $PEG_{3500}$/maleimide) in 100 mM sodium phosphate buffer/150 mM NaCl (pH 6.2) was added to 10 mg (2-3 mg/mL) of a preconjugate P/Gd-DOTA(15%)/MEA (5%) in the same buffer. After 1 hour at room temperature, the extend of the reaction was analysed by SEC-HPLC.

Alexa Fluor® 680 C2-maleimide (Alx 680) 1 mg in ml DMF was added and stirred for 1 h at RT. Remaining —SH-groups were blocked by adding excess of pyridyl(dithio)propionate (PDP) for 30 min at room temperature. After concentration over a centrifuge membrane filter Vivaspin 20, cutoff 30 kDa, 20 mL at 1500×g (Sartorius Stedim Biotech, Concord, Calif., USA), the final volume was adjusted to 2 ml before purification over Sephadex G-75 equilibrated with PBS, pH 7.4. Product containing fractions were isolated, combined and concentrated via membrane filtration. Reaction yield was 80-90%. FIG. 3 illustrates a synthesised Gd-DOTA-Polycefin nanoconjugate containing 15% Gd-DOTA, 0.25% Cetuximab, 0.25% anti-MsTfR mAb, 1% Alexa Fluor® 680 (Alx 680), 3.5% PDP and 70% pendant carboxyl groups. Results of Gd-analysis indicated 12% loading with regard to polymalic acid carboxyls. 12% loading corresponds to an average of 82 molecules of Gd loaded on each enhancer molecule.

Example 8. Characterization of Gd-DOT-Polycefin with Covalently Bound Cetuximab

Figure 4:
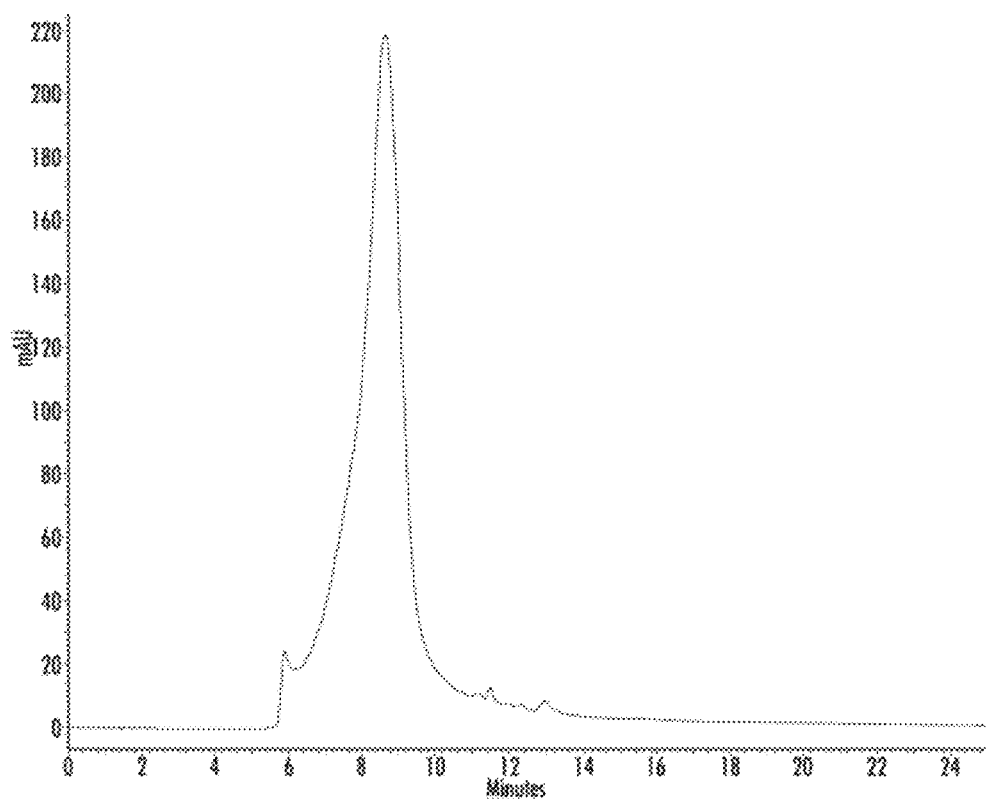
FIG. 4 illustrates the HPLC elution profile of the Gd-DOTA-Polycefin nanoconjugate containing Cetuximab.

Purity of the synthesized nanoconjugate was assessed by HPLC profiling. FIG. 4 depicts the elution profile of Gd-DOTA-Polycefin molecule carrying covalently bound Cetuximab. The detection was performed at 220 nm wavelength. Referring to FIG. 4, the position of the peak eluted as an early fraction (8 min) indicates a high purity and high molecular weight (Mw 470,000) of the nanoconjugate.

Figure 5:
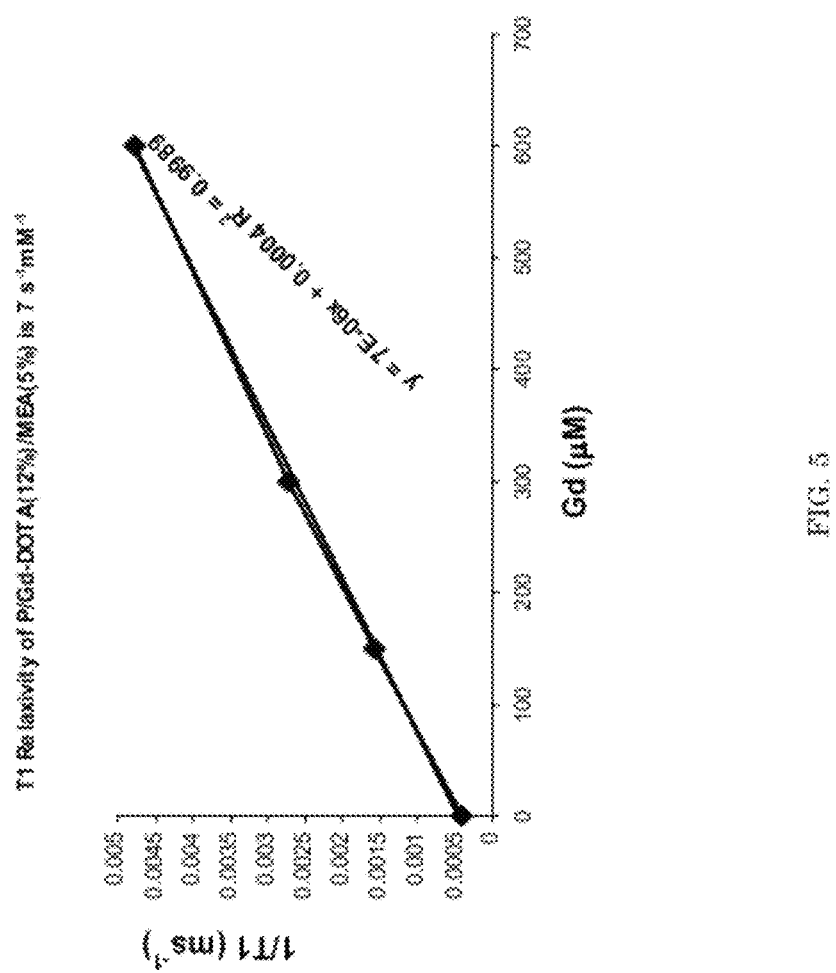
FIG. 5 is a set of line graphs illustrating calculation of T1-relaxivity for a Polycefin nanoconjugate that includes polymalic acid (P), 12% Gd-DOTA and 15% 2-mercaptoethane-1-amine (MEA).

FIG. 5 shows calculation of T1-relaxivity of Polycefin-Gd-DOTA(12%)-MEA(5%). Relaxivity refers to a measure of the ability of magnetic compounds to increase the relaxation rates of the surrounding water proton spins in nuclear magnetic resonance applications. Referring to FIG. 5, the T1 relaxivity value was calculated to be equal to 7 $s^{-1}mM^{-1}$. The calculated value is smaller than that of clinical MRI systems using a static magnetic field strength of 1.4 Tesla. A static magnetic field strength of the Siemens Microscan used was 9.4 Tesla. Relaxivity was calculated by measuring the slope of 1/T1 versus Gd concentration (μM). The equation Y=7E−0.6x+0.0004 allowed to translate absorbance at OD 450 directly to μM concentrations. The $R^2$ value equal to 0.9989 shows high accuracy of the calculation (with $R^2$ equal to 1 being perfect).

Figure 6:
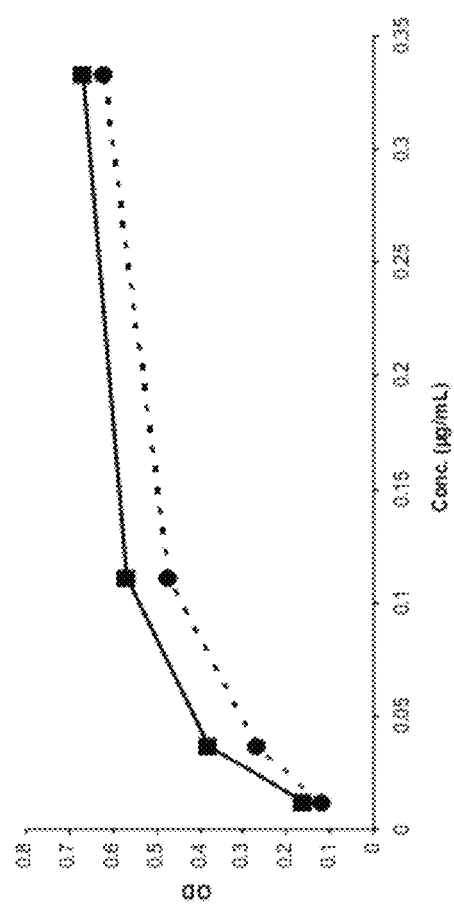
FIG. 6 is a set of line graphs illustrating affinity determination of monoclonal antibody specific to mouse transferrin receptor (anti-MsTfR mAb) by saturation ELISA. Solid line indicates free anti-MsTfR mAb. Broken line indicates MsTfR mAb attached to the Gd-DOTA-Polycefin nanoconjugate that also contains Cetuximab and AlexaFluor 680.

Affinity of ani-mouse TfR mAb to a target antigen (mouse-TfR) was determined by saturation ELISA (FIG. 6). The data shows that binding of a Gd-DOTA-Polycefin nanoconjugate containing Cetuximab, MsTfR and Alexa Fluor 680 was comparable to that o free anti-mouse TfR mAb. Reffering to FIG. 6, it was observed that the values of the dissociation constants of the antigen-antibody complexes were similar and in the range of 0.03 to 0.08 μg/mL corresponding to 0.2 nM to 0.5 nM. These values are close to published values and indicate that the antigen binding of anti-Mouse TfR mAb was not affected by its attachment to the Gd-DOTA-Polycefin nanoconjugate.

Figure 7:
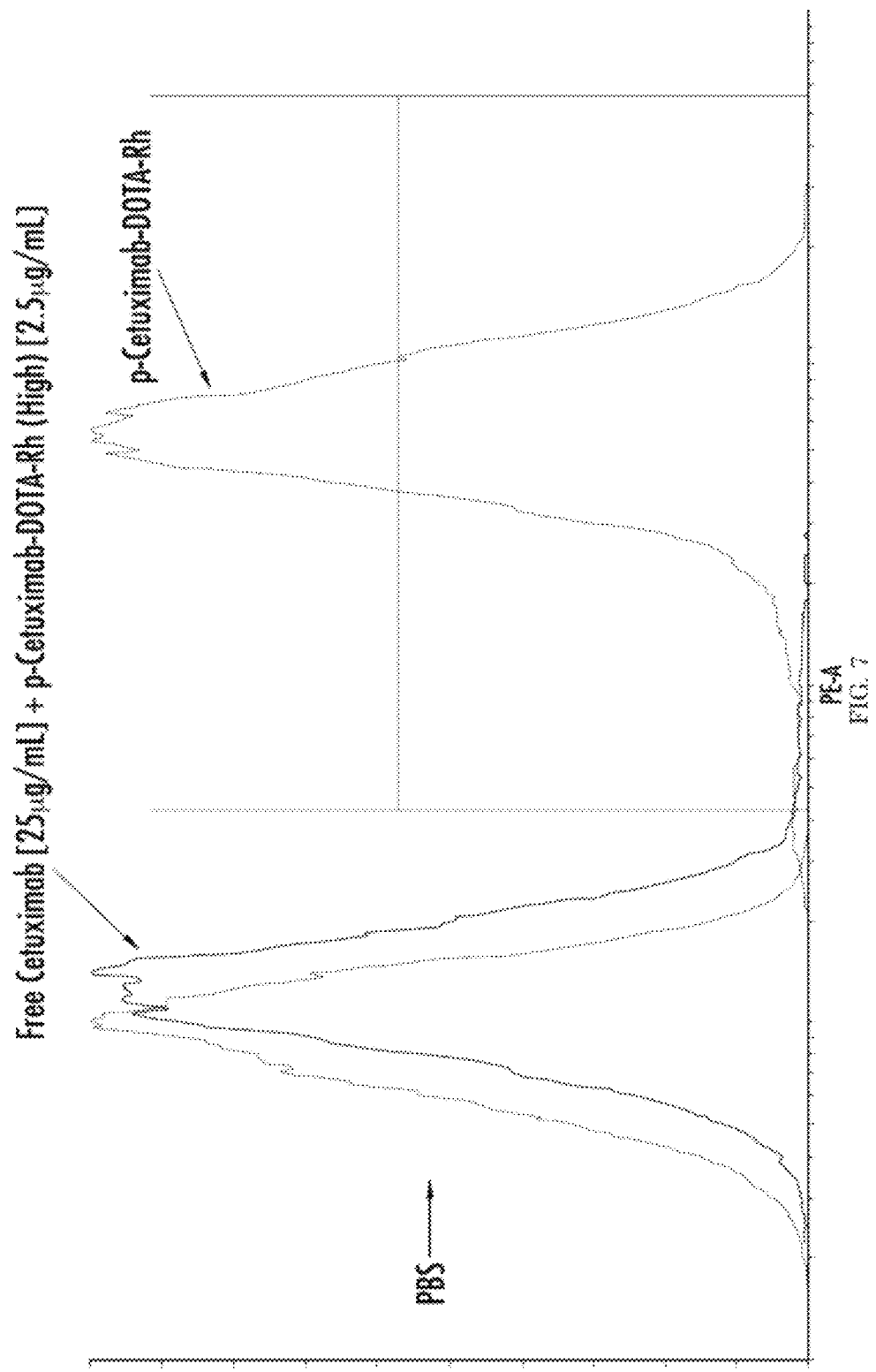
FIG. 7 is a set of Fluorescence Activated Cell Sorting (FACS) histograms illustrating binding of a Rhodamine-labelled Gd-DOTA-Polycefin nanoconjugate containing Cetuximab to an epidermal growth factor receptor (EGFR) expressed in MDA-MB-468 cells in comparison to free Cetuximab and phosphate buffered saline (PBS).

Specificity of Cetuximab to EGFR receptor was determined by Fluorescent Activated Cell Sorting (FACS) based on binding of Rhodamine-labelled Gd-DOTA-Polycefin-Cetuximab (2.5 μg/mL to EGFR expressed in MDA-MB-468 cells (amount 30,000) in comparison to that of phosphate buffered saline (PBS) (negative control) and free Cetuximab (positive control) (FIG. 7). This figure shows that the peak to the right corresponds to Rhodamine-labelled Gd-DOTA-Polycefin-Cetuximab bound to EGFR. In comparison, the peak the in the middle of histogram was found to correspond to free unlabeled Cetuximab at 25 μg/mL which did not bind EGFR. The positions of the peak corresponding to free unlabeled Cetuximab and the peak corresponding to that of the negative control PBS were very close.

Analysis data indicated that both anti-mouse TfR mAb and Cetuximab conjugated to Polycefin-Gd-DOTA preserved their functional activities and may be active during in vivo MRI.

Example 9. Materials and Methods for Tumor-Type Specific MRI

Cell Lines and Culture Conditions.

Human breast cancer cell line MDA-MB-468 (TNBC, EGFR positive) and human lung cancer cell line A549 (EGFR positive) were obtained from American Type Culture Collection (Manassas, Va.). Cells were cultured in L-15 and F-12K medium, respectively, supplemented with 10% FBS and antibiotic s/antimycotic s.

Tumor Xenografts in Nude Mice.

All experiments with animals were performed in accordance with the protocols approved by the Cedars-Sinai Medical Center Institutional Animal Care and Use Committee (IACUC). Athymic NCr-nu/nu mice were obtained from NCI-Frederick. MDA-MB-468 cells were stereotactically implanted at either $1.5 \times 10^6$ or $2.5 \times 10^6$ into the right basal ganglia field of mice. A549 cells were stereotactically implanted at $5 \times 10^5$.

Xenogen Fluorescent Imaging.

For the MRI and near infrared studies of contrast agent accumulation in the healthy brain and tumor tissue, the mice were anesthetized by inhalation of Isoflurane (2-4% to effect) inside an induction chamber. Once anesthetized, the mice were removed from the chamber; their tail was dipped in warm water to allow the vain to dilate and placed in a Mouse Tail Illuminator (Braintree Scientific Inc., Braintree, Mass.) to avoid failure of injection due to unexpected fast recovery from anesthesia. Contrast agent in PBS at a dose 0.1 mmol Gd/kg was administered via the tail vein of desired via the tail vein using a 30-gauge needle 1 ml syringe, at a rate of 100 μl within 5 seconds. (Single injection per mouse). Then, mice were anesthetized again by inhalation of Isoflurane (2-4% to effect) inside of an induction chamber before image detection. A nose cone was placed to maintain anesthesia during MRI measurements. During measurements, 1.8% isoflurane was maintained. The mouse bed was heated to prevent cooling of the mice during anesthesia.

MRI Measurement.

The MRI sessions were performed on a Siemens Microscan System 9.14 Tesla, 45 after (for A549) and 27, 48 and 52 days after (for MDAMB 468) cell inoculation when tumors were ~4 mm in diameter. Spin echo and T1 images of the entire brain were acquired. Axial slices were positioned over the entire brain. A multisided echo sequence was used with TR=900 ms. 50 Slices with a 0.5 mm thickness were acquired for a 1.8×1.8 cm field of view with a 196×196 matrix size. The in-plane resolution was 92×92 μm/pixel. T1 values of the samples were measured from regions of interest using a single exponential fitting of the intensity for different repetition times scans. In this case, the in-plane resolution was 234×234 μm/pixel.

Xenogen IVIS 200 Imaging.

For the assessment of drug distribution and localization in nude mice, animals were studied in a Xenogen IVIS 200 imager under isoflurane anesthesia at different time points (before drug administration and 24 h after the injection of the drug). Twenty-four hours after drug administration, mice were euthanized. Intra-arterial PBS perfusion was done in order to wash out the circulating drugs in blood vessels. The tumor and major organs were harvested to detect the fluorescent signal. The fluorescent signal intensities in the tumor and different organs were analyzed by Xenogen Living ImageH software, Version 2.50 (WaveMetrix, USA).

Example 10. MRI-Enhancement by Gd-DOTA-Polycefin

Figure 8:
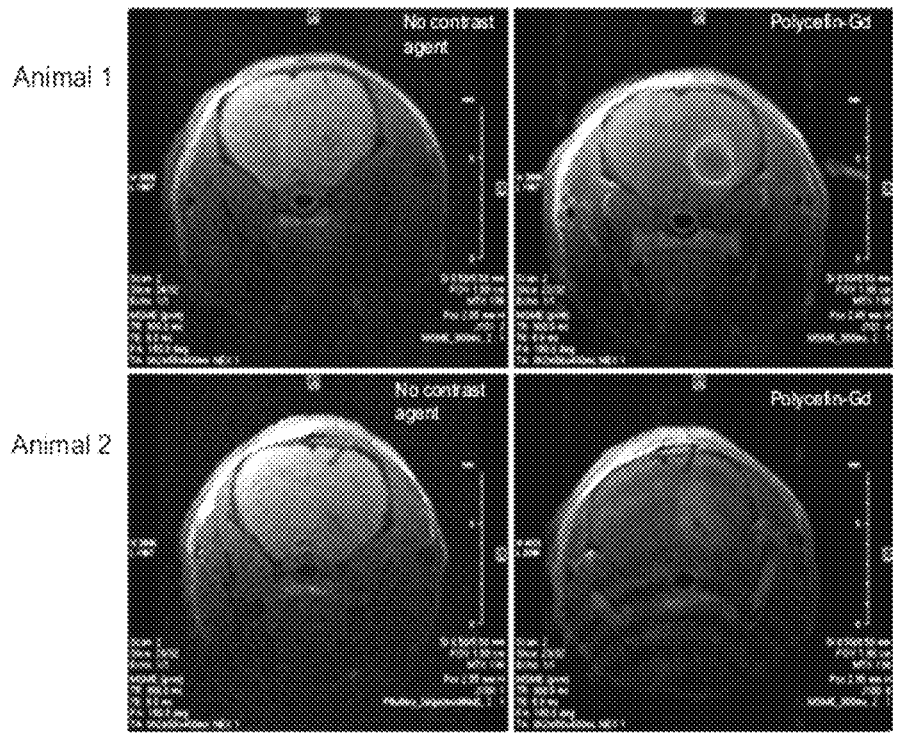
FIG. 8 is a set of MRI images showing brain sections of mice having TNBC metastatic tumors. Images on the left were obtained without a contrast agent administered to animals. Images on the right were obtained after animals received a Polycefin-Gd nanoconjugate intravenously. Scale bar=50 µm.

Initial experiments with TNBC tumor A549 were negative due to insufficient Gd-DOTA bound to polymalic acid in a Polycefin nanoconjugate (less than 5%), % refers to the fraction of total carboxyls of the polymalic acid platform covalently bound to Gd-DOTA. Subsequent experiments were conducted with Gd-DOTA-Polycefin loaded with 12-13% Gd. FIG. 8 shows the result of imaging of two animals representing mouse model of TNBC injected with the human TNBC-specific MRI enhancer nanoconjugate. MRI imaging of human TNBC on mouse was performed 27 days after tumor inoculation. Referring to FIG. 8, it was observed that animals injected with a Polycefin-Gd nanoconjugate displayed considerable accumulation of Polycefin-Gd in tumors which made tumors visible. In contrast, no tumors were visible on images of animals which were not injected with the contrast agent. The data shows feasibility of MR imaging using a Polycefin-Gd nanoconjugate.

FIG. 9 shows MR imaging of the animals having the same type of tumors as shown in FIG. 8 using a Polycefin-Gd nanoconjugate and a commercially available Gd(III) enhancer reagent. However the time of injection of Gd(III) enhancer reagents were 49-52 days after tumor inoculation. This tumor MRI was used for to time dependent evaluation. Top images show administration of Gd(III) for clinical use. Top image on the left was made 15 minutes after reagent injection and shows visible tumor. Top image on the right was made 1 hour 40 minutes after injection of Gd (III) and does not show tumor image, because Gd(III) enhancer reagent was already cleared through the kidneys. Bottom images show administration of a Gd-DOTA-Polycefin nanoconjugate specific for EGFR expression on TNCB cells. Lower image on the left was made 15 minutes after injection of P/Gd-DOTA/MsTfR/Cetux/Alx680 nanoconjugate and shows visible tumor. Lower image on the right was made 3 hours 15 minutes after injection of the nanoconjugate. The data indicates that the enhancement effect of Gd-DOTA-Polycefin is retained for much longer time than that of the Gd(III) reagent routinely used in clinics. This prolongation may be explained by an effect of slower clearance through the kidneys as it takes longer to clear the nanoconjugate because of its high molecular weight above clearance cutoff, and retention of the polymer bound Gd(III) because of tumor specific binding.

Figures 10A, 10B:
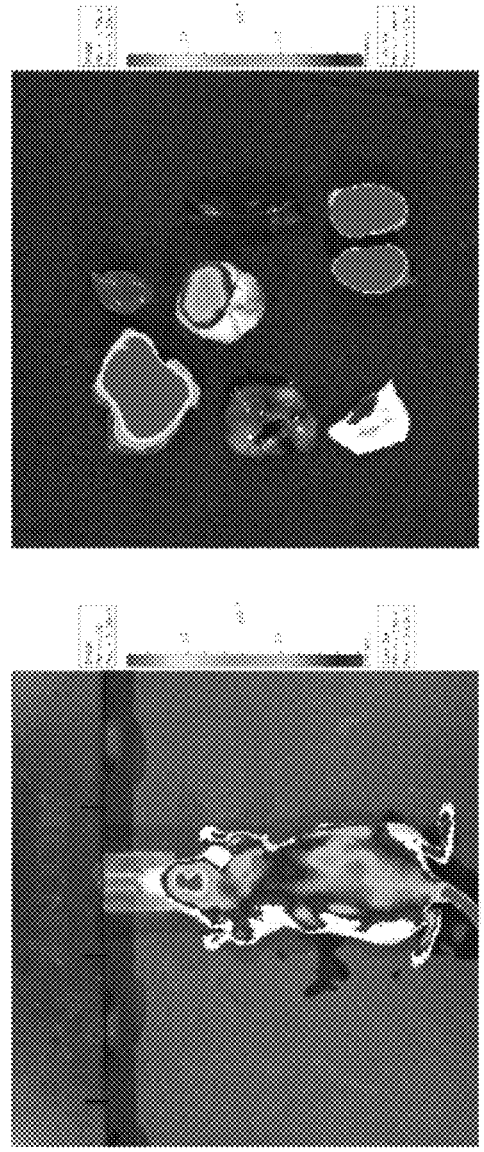
FIGS. 10A and 10B illustrate Xenogen fluorescence imaging of animals injected with a Polycefin-Gd-DOTA nanoconjugate containing Gd-DOTA, MsTfR, Cetuximab Alexa Fluor 680 dye.

To evaluate specific localization of accumulated enhancement reagents within a body of an experimental animal, Alexa Fluor 680 was attached to a Gd-DOTA-Polycefin nanoconjugate for Xenogen imaging using fluorescence. Referring to FIGS. 10A-10B, the image on FIG. 10A demonstrates high amounts of imaging agent accumulated in kidneys and liver of an animal. The image on FIG. 10B shows tumor in the middle identifiable by blue fluorescence and accumulation of Polycefin-Gd-Alexa Fluor 680.

Example 11. Evaluation of Specificity of MRI Enhancement Reagents

To separate the retention effect based on binding to target from the prolonged natural clearance effect through the kidneys the kinetics of the T1-values were evaluated.

Figure 11:
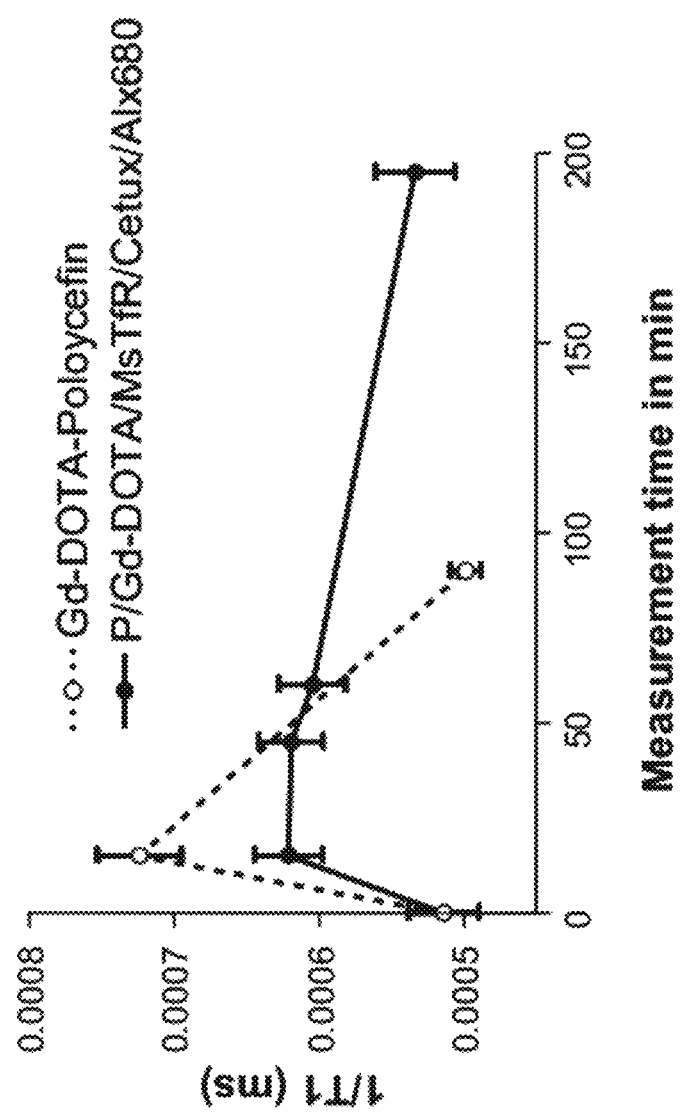
FIG. 11 is a set of line graphs illustrating MRI kinetics for tumors after injecting to animals clinically used Gd (III) (open circles) and a Polycefin nanoconjugate containing Gd-DOTA, MsTfR, Cetuximab and Alexa Fluor 680 (closed circles).

FIG. 11 shows kinetics of MR imaging after injecting the subject with clinically used formulation of Gd(III) and formulation of a Gd-DOTA-Polycefin nanoconjugate carrying covalently bound Cetuximab. The kinetics of imaging was not deconvoluted and contain effects of different blood clearance times due to different molecular weights and, in the case of Gd-DOTA-Polycefin retention by interaction of covalently bound Cetuximab with EGFR on tumor cell surface. Referring to FIG. 11, it was observed that the high values of 1/T1 were maintained for several hours for Polycefin-Gd-DOTA while the curve for clinical Gd(III) rapidly decayed after reaching a maximum value. The differences in kinetics profiles may be explained by the fact that the 1/T1 value depends on the amount of clinical Gd(III) or Polycefin bound Gd(III) in the circulating blood; and on the retention of Polycefin-Gd-DOTA by the tumor. Clinical Gd(III) cannot penetrate BBB and is not retain by the tumor, and may only circulate in the tumor blood capillaries. The levels of both a clinically used Gd(III) and Polycefin-Gd-DOTA decrease because of clearance through kidneys. However, the clearance of Polycefin-Gd-DOTA is slower than that of clinically used Gd(III) because large molecules, such as Polycefin-Gd-DOTA are less rapidly cleared.

FIGS. 12A and 12B compares kinetics of T1 relaxation of MRI for healthy and tumor areas of brain after injection of clinically used Gd(III) enhancer reagent and a Gd-DOTA-Polycefin nanoconjugate containing Cetuximab. FIG. 12A shows that after application of Gd(III) 1/T1 values obtained for a healthy and tumor areas of brain are not significantly different for 50 minutes following the injection of the contrast agent. The data may be explained by the fact that the Gd(III) formulation does not recognize the tumor. FIG. 12B shows that 1/T1 values obtained for a healthy and tumor areas of brain after injection of the Gd-DOTA-Polycefin nanoconjugate containing Cetuximab are significantly different. Half-life of the nanoconjugate in the healthy area of brain is 20-30 minutes and that in the tumor area is 130 minutes. The higher half-time value obtained for the noconjugate in the tumor area may be explained by retention of the nanoconjugate by tumor due to specific binding of the nanoconjugate to EGFR.

Example 12. MRI-Enhancing Reagents Targeting Different Types of Tumors

Figure 13A:
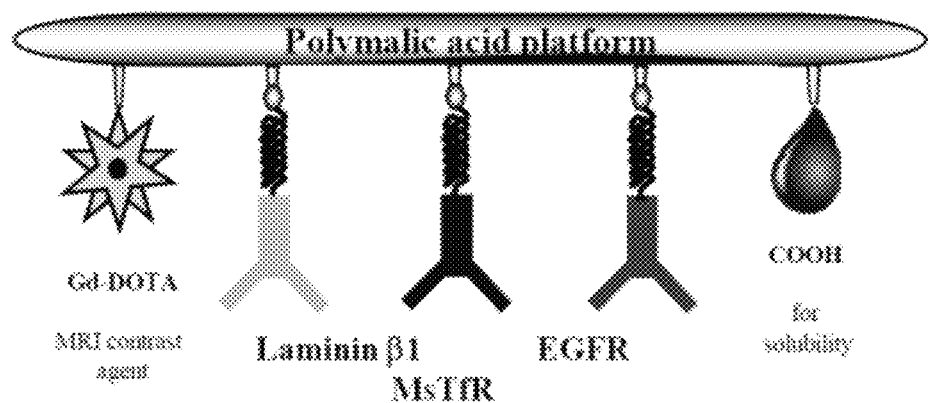
FIGS. 13A to 13D are a set of schematic drawings illustrating nanoconjugates designed to target primary brain and TNBC metastasized to brain (FIG. 13A), and HER2 positive breast cancer metastasized to brain (FIG. 13B) glioblastoma (FIG. 13C), in comparison to a control molecule lacking specific targeting modules (FIG. 13D).
Figure 13B:
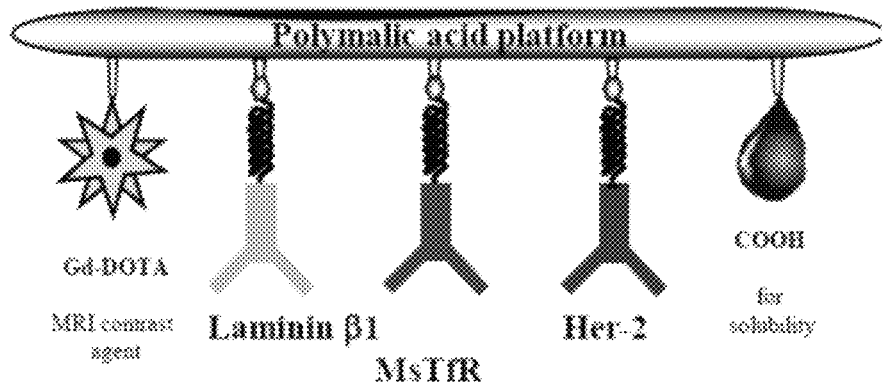
Figure 13C:
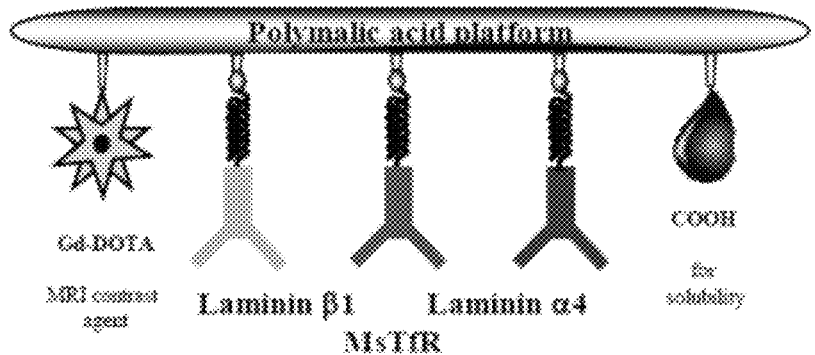
Figure 13D:
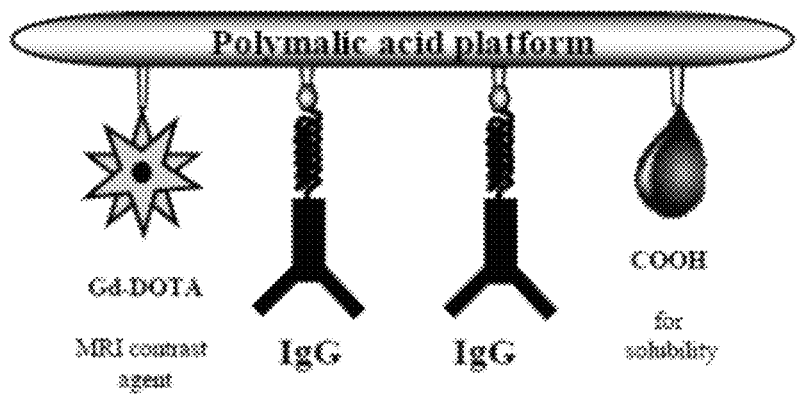

Imaging of different types of tumors involves formulation of nanoconjugates having an ability to target tumors specifically and differentiate between different types of tumors. FIGS. 13A-13D show schematic drawings of molecules designed to target primary brain and TNBC metastasized to brain (FIG. 13A), HER2-positive brain cancer metastasized to brain (FIG. 13B), glioblastoma (FIG. 3C) and a control molecule lacking specific targeting modules (FIG. 13D). All nanoconjugates of FIGS. 13A-13D were designed for targeting specific tumors and a control molecule include Gd-DOTA, as an MRI contrast agent for MRI, and having a carboxyl group COOH for improving solubility, where each of these moieties attached to polymalic acid platform. Referring to FIG. 13A, a nanoconjugate designed for targeting and imaging primary brain and metastatic brain tumor of triple negative breast cancer includes mAbs for targeting: mAb specific to laminin β1, MsTfR mAb and Cetuximab specific to EGFR. Referring to FIG. 13B, a nanoconjugate designed to target and facilitate imaging of HER2 positive breast cancer metastasized to brain includes mAbs for targeting: mAb specific to laminin β1, Herceptin® specific to HER2 and TfR mAb. Referring to FIG. 13C nanoconjugate designed to target and facilitate imaging of glioblasoma includes mAbs for targeting: mAb specific to laminin β1, mAb specific to laminin α4 and MsTfR mAb.

Referring to FIG. 13D, a nanoconjugate designed as a control for other agents includes mouse mAbs for targeting: two IgG1 monoclonal antibodies that do not bind specific targets in tumors.

Validation of specific effect of the nanoconjugates on MRI is performed on mouse models of TNBC, the HER2-positive breast cancer metastasized to brain and glioblastoma. These models may also be used to differentiate specific and non-specific effects of the nanonoconjugates on MRI. For example, although the nanoconjugates are designed for binding to specific targets, unspecific penetration of the nanoconjugates may occur through the permissive (while damaged) endothelia of BBB called a typical tumor effect due to an "enhanced permeation and retention" (EPR). Images obtained after application of nanoconjugates designed for specific targets will be compared with control images. Together the results will indicate the strength of specificity and the "background" effect of injection of the control molecule, in which specific targeting modules are replaced with IgG1 mAbs. The background effect is of interest for translation into the human system since in human tumors, transferrin receptors are typically present in capillary endothelia and on tumor cell surface. A tumor specificity may be improved by eliminating the anti-human Tfr mAb and relying only on the EPR effect for penetration of BTB and targeting cancerous tissues.

Example 13. MRI Enhancing Reagent Targeting Alzheimer Plaques

An MRI enahancing nanoconjugate was designed to image Alzheimer plaques. Previously it was shown that curcumin can bind beta amyloid plaque (Ryu E K et al. 2006 J Med Chem 49: 6111).

Figure 14:
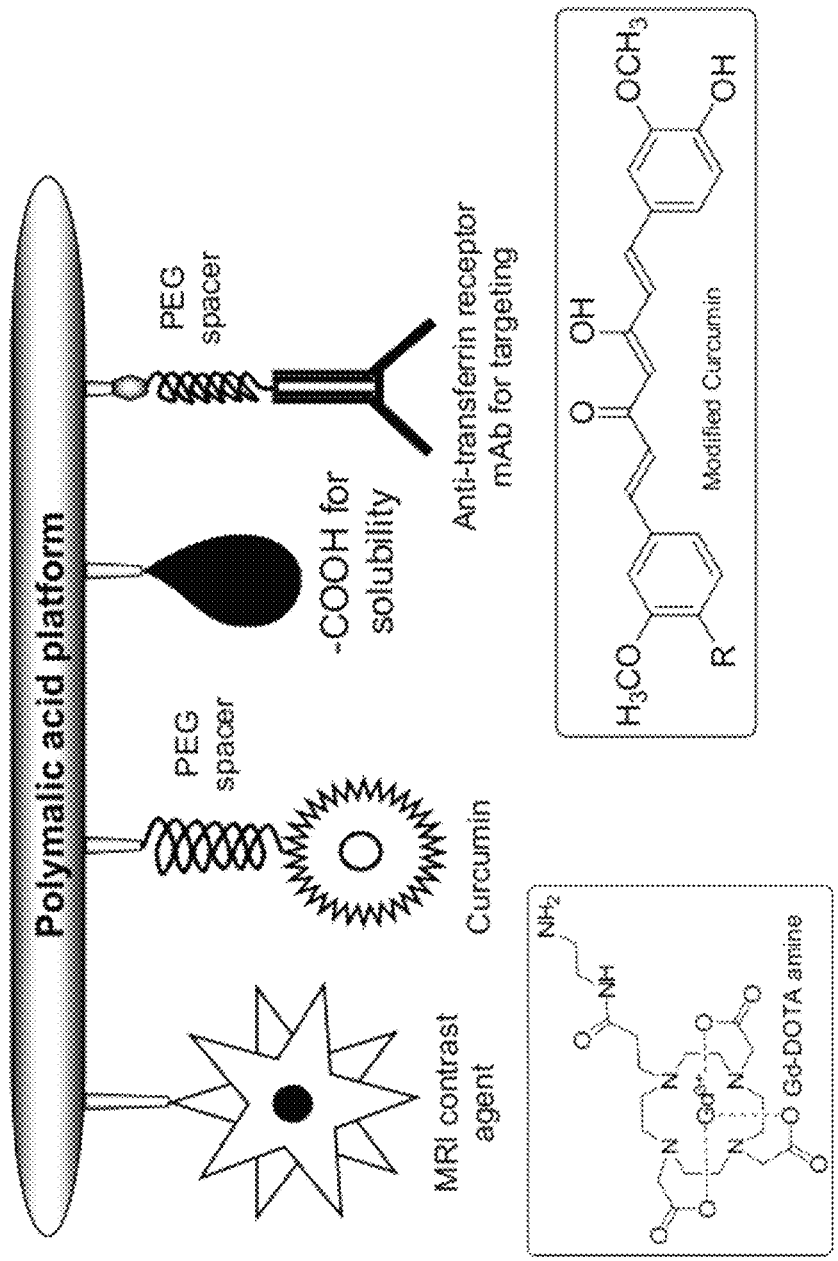
FIG. 14 is a schematic drawing illustrating a nanoconjugate designed to facilitate imaging of Alzheimer's plaques.

A nanoconjugate based on polymalic acid contains simultaneously attached curcumin (5-hydroxy-1,7-bis(4-hydroxy-3-methoxyphenyl)-1,4,6-heptatrien-3-on) and Gd-DOTA (2,2',2"-(2-(2-(2mercaptoethylamino)-2-oxoethyl)-1,4,7-tet-raazacyclododecane-4,4,7-triyl)triacetic acid), and is designed to target and image Alzheimer's disease beta-amyloid plaques in vivo (FIG. 14). The nanoconjugate is a composite molecule containing features of Polycefin and the following chemically functional modules: an MRI contrast agent Gd-DOTA, curcumin for binding amyloid plaques, a carboxy group and TfR specific mAb attached to polymalic acid. Each of curcumin and TfR mAb modules is linked to polymalic acid by the PEG spacer.

To study in vivo imaging in mouse and rat models of Alzheimer's disease (AD models), mouse or ratTfR mAb could be used. Mouse or rat TfR could be replaced with human TfR for imaging in human patients. A nanoconjugate can carry multiple curcumin molecules which may result in firm attachment of a nanoconjugate around beta-amyloid plaque contributing to sharp contours with high contrast. Nanoconjugate molecules containing curcumin can also carry a large number of covalently attached Gd-DOTA, typically 40-60 or more Gd per molecule of nanoconjugate. This high concentration of Gd on amyloid plaques may allow imaging by MRI at high contrast and resolution quality. The optional covalent attachment of a tracking dye may facilitate gross in vivo monitoring of the nanoconjugate distribution by Xenogen imaging systems other than by using MRI and may allow the validation of curcumin-Polycefin (Gadolinium absent) entrance into brain in the first phase of the synthesis/investigation. A tracking dye may also validate whether curcumin is attached to Polycefin within the brain. Thus, it can be useful in optimization experiments with curcumin-Polycefin in the absence of Gd.

If curcumin binding is not sufficiently strong, an antibody that specifically recognizes human Alzheimer plaques may be used. Penetration of the enhancement reagent may be accomplished by the attached anti-transferrin antibody (anti-TfR mAb), which carries the enhancer through the BBB by transcytosis. Because BBB transcytosis is reversible, the enhancer reagent could be very firmly attached to the plaques. If curcumin does not bind sufficiently strong, the plaque-specific mAb may be attached to the platform instead of curcumin. Multiple curcumin residues attached to the platform may enhance the strength of plaque binding through multiple binding. If further strength enhancement is designed an alternative of using the antibody may be employed.

Example 14. General Procedure for N-Alkylation

Figure 15:
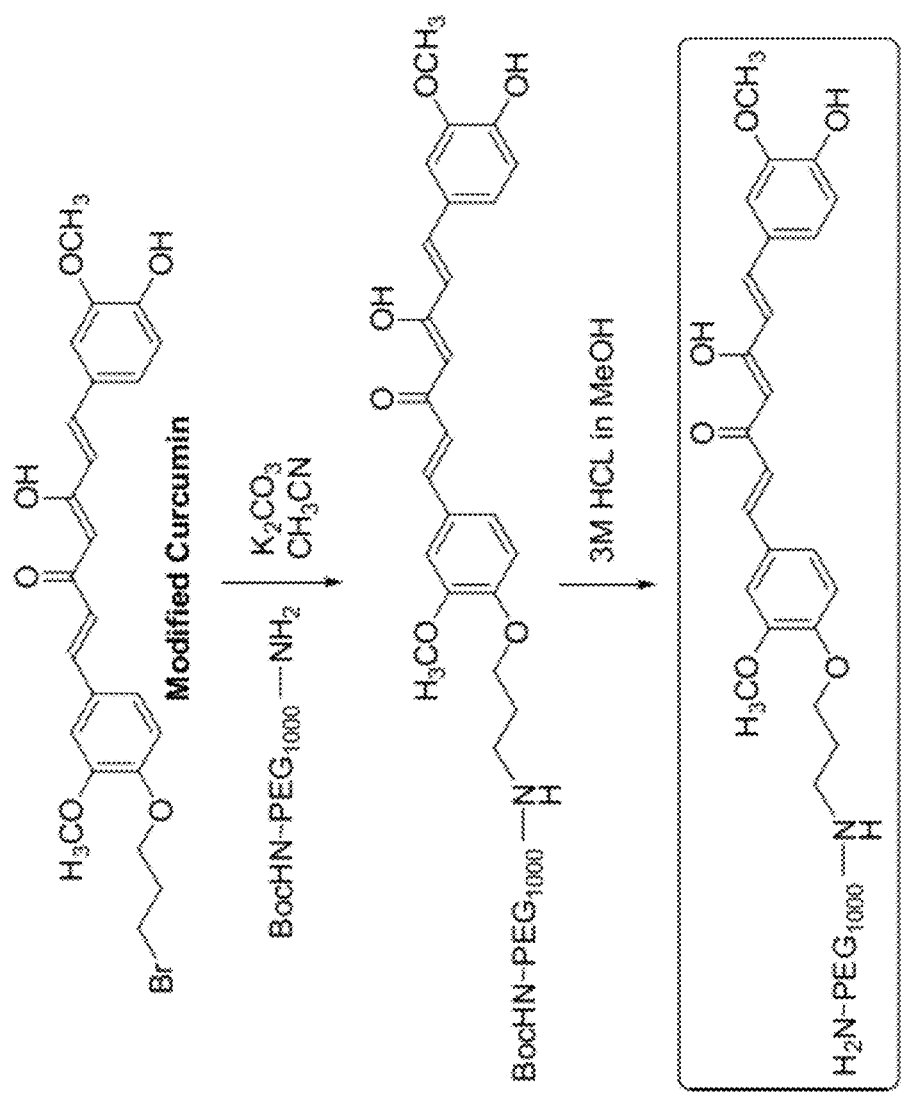
FIG. 15 is a diagram illustrating synthesis of a curcumin-$PEG_{1000}$-amine.

FIG. 15 shows synthesis of a curcumin-PEG$_{1000}$-amine. A solution of Boc-PEG$_{1000}$-NH$_2$ (0.2 mmol) in 2 ml of acetonitrile was added to a suspension of K$_2$CO$_3$ (1.2 mmol) in 2 ml acetonitrile, and the reaction mixture was stirred at room temperature for 10 min. A solution of modified curcumin (0.2 mmol) in 2 ml acetonitrile was added to the reaction mixture, and the reaction was allowed to proceed at RT for 72 hours. The reaction mixture was filtered to remove undissolved solids and washed with acetonitrile. The filtrate was concentrated and the residue was passed over sephadex LH 20 in methanol. Product containing fractions were collected, methanol was removed. Product was used for next step without further purification. Reaction yield was 73%.

Example 15. General Procedure for Boc Deprotection 3M methanolic HCL 9 ml was added to Boc-NH-PEG$_{1000}$-curcumin and reaction mixture was stirred at room temperature for 16 hour. Solvent was evaporated to dryness with rotary evaporator. Thick solid was dissolved in water and freeze dried to obtain a desired product as dark yellow solid. Reaction yield 96%.

Figure 16:
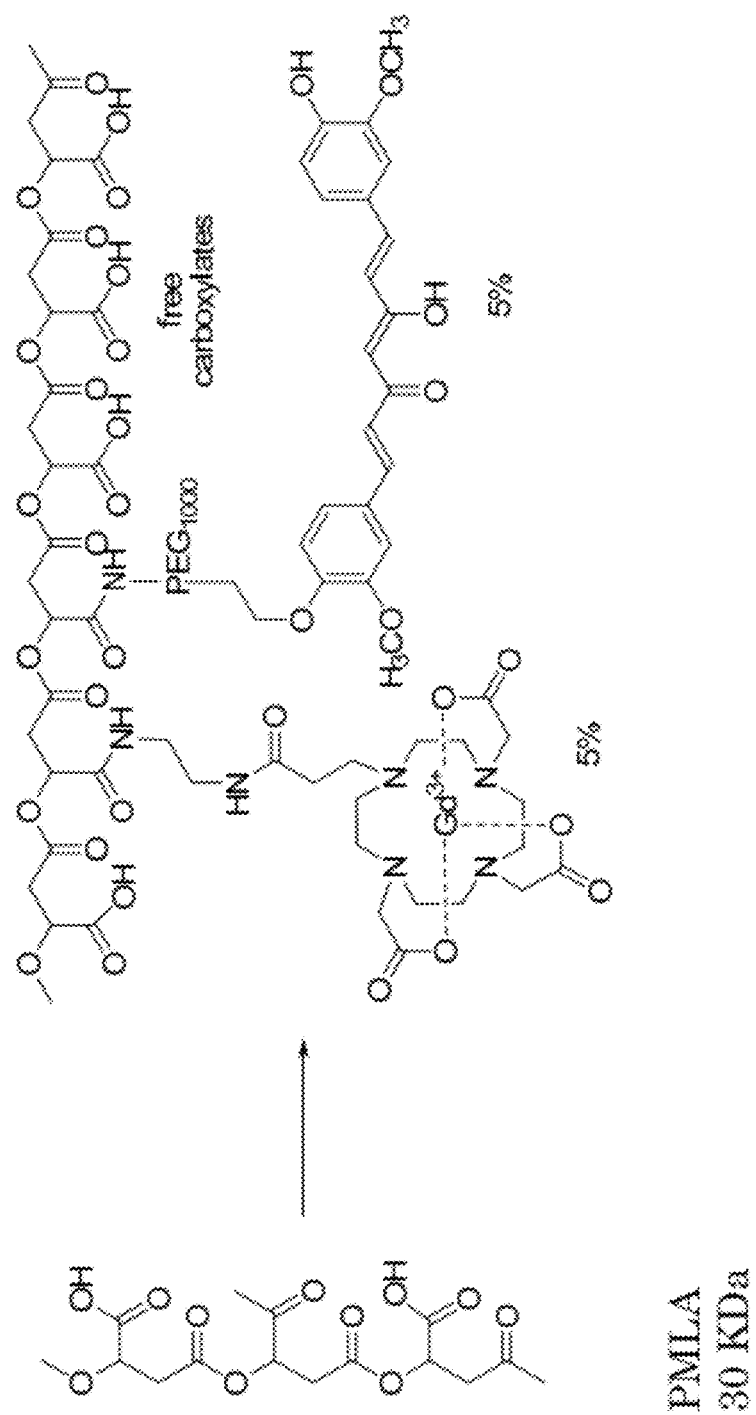
FIG. 16 is a diagram illustrating attachment of curcumin and Gd-DOTA modules to polymalic acid.

The curcumin derivatives will be covalently attached to NHS-activated carboxyls of polymalic acid together with 2-mercapto-1-ethylamin and Gd-DOTA to receive the MRI-enahcer as shown in FIG. 16. In this figure, curcumin and Gd-DOTA are shown to be attached to polymalic acid (PMLA, 30 KDa). Each of curcumin and Gd-DOTA is attached to 5% of polymalic acid pendant carboxylates. The percentage of attached modules may be increased up to 30% or more of pendant carboxylates to improve MRI enhancement of the reagent.

Example 15. Binding of Polymalic Acid-Bound Curcumin (5%)

Figure 17:
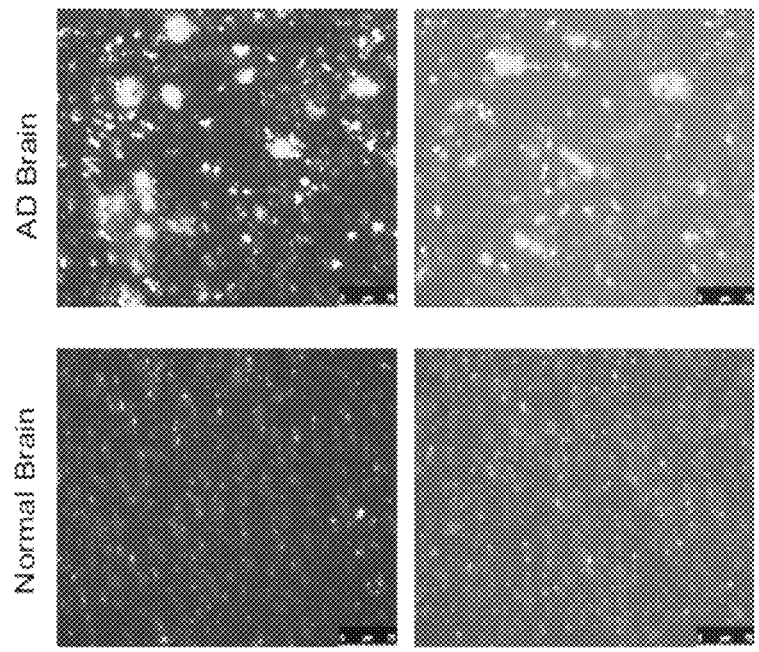
FIG. 17 is a set of photographs of fluorescent microscopy of slices of human brain having AD (top images) and normal (bottom images) stained with 20 µM of free curcumin (right) and 20 µM of a Polycefin-curcumin nanoconjugate (left).

Polymalic acid-bound curcumin can be used to stain plaques in human brain tissue ex vivo (FIG. 17). Slices of human brains having AD (top images) and normal hunan brains (lower images) were analyzed by fluorescent imaging after staining with 20 μM of Polycefin-curcumin (images to the right) and 20 μM of free curcumin (images to the left). Referring to FIG. 17, the higher number of bright light spots observed on the top left image compared to that on the top right image indicates stronger binding of the polymalic acid-curcumin conjugate than of free curcumin to human Alzheimer plaques in slices of brain obtained from a patient having Alzheimer disease (AD). No binding occurred in control that included slices of brain obtained from a healthy individual as visible on the lower images. Concentration of a polymalic acid curcumin conjugate may be reduced to 2 µM. The use of polymalic acid-curcumin is advantageous compared to the used of free curcumin because it does not show staining background even at high concentrations, such as higher than 200 µM. This demonstrates that binding to polymalic acid greatly enhances the solubility of curcumin.

Example 16. Diagnosing and Monitoring Alzheimer's Disease

The nanoconjugate Gd-DOTA/polymalic acid/Curcumin (5%)/anti-mouse TfR mAb may be used as MRI enhancer for imaging the plaques. The strategy for imaging may also include replacing of Gd-DOTA by the highly fluorescent dye AlexaFluor 680 and finding conditions that allow detection of fluorescence in the brain of Alzheimer-mouse using Xenogen Imaging System. Curcumin may also be replaced by anti-plaque mAb. For detection by fluorescence, the MRI system using Gd-DOTA (highest possible %)/polymalic acid/Curcumin or anti-plaque antibody/anti-TfR mAb for imaging.

The references cited throughout this application, are incorporated for all purposes apparent herein and in the references themselves as if each reference was fully set forth. For the sake of presentation, specific ones of these references are cited at particular locations herein. A citation of a reference at a particular location indicates a manner(s) in which the teachings of the reference are incorporated. However, a citation of a reference at a particular location does not limit the manner in which all of the teachings of the cited reference are incorporated for all purposes.

It is understood, therefore, that this invention is not limited to the particular embodiments disclosed, but is intended to cover all modifications which are within the spirit and scope of the invention as defined by the appended claims; the above description; and/or shown in the attached drawings.

The invention claimed is:

1. A method of targeting and imaging a cell or a tissue in a brain of a subject comprising:
    administering to the subject a composition including a polymalic acid-based molecular scaffold having a plurality of pendant carboxyl groups, at least one imaging moiety, and at least one targeting module, wherein the polymalic acid-based molecular scaffold is a homopolymer, each of the at least one imaging moiety is conjugated to the polymalic acid-based molecular scaffold through one of the plurality of the pendant carboxyl groups, each of the at least one targeting module is conjugated to the polymalic-acid based molecular scaffold through one of the plurality of the pendant carboxyl group, the at least one imaging moiety comprises Gd-DOTA, the at least one targeting module comprises Cetuximab, and the polymalic acid-based molecular scaffold comprises polymalic acid having a molecular weight between 10,000 Daltons and 800,000 Daltons, and from 5% to 30% of the plurality of the pendant carboxyl groups are conjugated to the Gd-DOTA by an ethylene diamine linker, and the composition is capable of crossing a blood-brain barrier after administering to the subject;
    visualizing the at least one imaging moiety in the brain of the subject by a magnetic resonance imaging technique; and
    differentially diagnosing a primary brain cancer from a metastatic brain cancer or a non-tumorous lesion in the brain of the subject.

2. The method of claim 1, wherein the metastatic brain cancer is selected from the group consisting of: triple negative breast cancer metastasized to the brain, lung cancer metastasized to the brain, and HER2-positive breast cancer metastasized to the brain.

3. The method of claim 1, wherein the primary brain cancer is glioblastoma.

4. The method of claim 1, wherein each of the at least one targeting module is independently selected from a group consisting of: an antibody, a peptide, a polypeptide, an oligonucleotide, and a therapeutic chemical.

5. The method of claim 1, wherein the at least one targeting module targets a diseased cell or a diseased tissue and the step of administering results in reduction or elimination of at least one symptom of a disease or condition.

6. The method of claim 5 further comprising monitoring an efficiency of treatment of a disease or other condition in the subject comprising: obtaining a first image of the cell or the tissue in the subject after the step of administering at a first time; obtaining a second image of the cell or the tissue after a period of time subsequent to the first time; and comparing the first image and the second image.

7. The method of claim 1 further comprising providing a period of time for accumulation of the composition in a diseased cell or a diseased tissue.

8. The method of claim 4, wherein the antibody specifically binds to a protein selected from the group consisting of: an epidermal growth factor receptor, laminin 411, insulin-like growth factor, transferrin receptor protein, and tumor necrosis factor-alpha.

9. The method of claim 1, wherein differentially diagnosing comprises determining the presence of the primary brain cancer, the metastatic brain cancer or the non-tumorous lesion in the brain of the subject, wherein determining comprises obtaining a first MRI image of the cell or the tissue in the brain of the subject after the step of administering at a first time; measuring the intensity of an MRI signal in the first image; and comparing the intensity of the MRI signal in the first image with the intensity of the MRI signal in a control MRI image of a normal cell or a tissue from a healthy individual, wherein the a difference in the intensity in the MRI signal in the first MRI image relative to the control MRI image is indicative of the presence the primary brain cancer or the metastatic brain cancer.

10. The method of claim 9 further comprising determining a tumor type, wherein determining comprises
    obtaining a second MRI image of the cell or the tissue a second time after a period subsequent to the first time;
    measuring the intensity of the MRI signal in the second MRI image; and
    comparing the intensity of the MRI signal in the first MRI image with the intensity of the MRI signal in the second MRI signal, wherein the intensity of the MRI signal in the second MRI image similar to the intensity of the MRI signal in the first MRI image is indicative of the presence of an EGFR-expressing tumor.

11. The method of claim 10, wherein the EGFR-expressing tumor is at least one tumor selected from the group consisting of: triple negative breast cancer metastasized to the brain, lung cancer metastasized to the brain, and glioblastoma.

12. The method of claim 1, wherein the non-tumorous lesion is caused by infection resulting from impairment of the immune system.

* * * * *